(12) United States Patent
Cushman et al.

(10) Patent No.: US 9,328,073 B2
(45) Date of Patent: May 3, 2016

(54) ALCOHOL-, DIOL-, AND CARBOHYDRATE-SUBSTITUTED INDENOISOQUINOLINES AS TOPOISOMERASE I INHIBITORS

(75) Inventors: Mark S. Cushman, West Lafayette, IN (US); Yves George Pommier, Bethesda, MD (US)

(73) Assignee: Purdue Research Foundation, West Lafayette, IN (US)

( * ) Notice: Subject to any disclaimer, the term of this patent is extended or adjusted under 35 U.S.C. 154(b) by 77 days.

(21) Appl. No.: 14/119,673

(22) PCT Filed: May 24, 2012

(86) PCT No.: PCT/US2012/039365
§ 371 (c)(1),
(2), (4) Date: Nov. 22, 2013

(87) PCT Pub. No.: WO2012/162513
PCT Pub. Date: Nov. 29, 2012

(65) Prior Publication Data
US 2015/0148370 A1 May 28, 2015

Related U.S. Application Data

(60) Provisional application No. 61/489,900, filed on May 25, 2011.

(51) Int. Cl.
*C07D 221/18* (2006.01)
*C07D 311/94* (2006.01)

(52) U.S. Cl.
CPC ............ *C07D 221/18* (2013.01); *C07D 311/94* (2013.01)

(58) Field of Classification Search
None
See application file for complete search history.

(56) References Cited

U.S. PATENT DOCUMENTS

| 5,627,165 | A | 5/1997 | Glazier |
| 2004/0229895 | A1 | 11/2004 | Jagtap et al. |
| 2008/0262016 | A1 | 10/2008 | Jagtap et al. |
| 2008/0318995 | A1 | 12/2008 | Cushman et al. |

FOREIGN PATENT DOCUMENTS

EP   2050452 A1   4/2009

OTHER PUBLICATIONS

Wawzonek, S., 14(3) Org. Prep. & Proc. Int'L 163-8 (1982) (citing CAS Abstract).*
Strumberg et al., 42(3) J. Med. Chem. 446-457 (1999) (CAS Abstract).*
Antony et al. "Novel indenoisoquinolines NSC 725776 and NSC 724998 produce persistent topoisomerase I cleavage complexes and overcome multidrug resistance", Cancer Res. Nov. 1, 2007;67(21):10397-405.
Dexheimer et al. "DNA cleavage assay for the identification of topoisomerase I inhibitors", Nat Protoc. 2008;3(11):1736-50. doi: 10.1038/nprot.2008.174.
Finch et al., "The structures of D-arabinose and D-glucose oximes", Journal of the Chemical Society-Perkin Transactions 1 1975, 1682-1686.
International Search Report for PCT Application No. PCT/US12/39365 mailed Oct. 6, 2014.
Ley et al."Tetrapropylammonium Perruthenate, Pr4N+RuO4-, TPAP: A Catalytic Oxidant for Organic Synthesis", Synthesis 1994, 639-666.
Morrell et al. "Synthesis of nitrated indenoisoquinolines as topoisomerase inhibitors", Bioorg Med Chem Lett. Jul. 16, 2004;14(14):3659-63.
Morrell et al. "A systematic study of nitrated indenoisoquinolines reveals a potent topoisomerase I inhibitor", J Med Chem. Dec. 28, 2006;49(26):7740-53.
Pathalk et al. "Enzymic protecting group techniques in organic synthesis", Stereosel. Biocatal. 775-797 (2000) in Stereoselective biocatalysis, edited by Ramesh N. Patel, Ch. 26.
Paull et al. "Display and analysis of patterns of differential activity of drugs against human tumor cell lines: development of mean graph and COMPARE algorithm", J Natl Cancer Inst. Jul. 19, 1989;81(14):1088-92.
Peterson et al. "Alcohol-, diol-, and carbohydrate-substituted indenoisoquinolines as topoisomerase I inhibitors: investigating the relationships involving stereochemistry, hydrogen bonding, and biological activity", J Med Chem. Jul. 28, 2011;54(14):4937-53.
Pommier et al. "The indenoisoquinoline noncamptothecin topoisomerase I inhibitors: update and perspectives.",Mol Cancer Ther. May 2009;8(5):1008-14.
Snyder "An N.M.R. investigation of the aldopentose oximes", Carbohydrate Research, vol. 198, Issue 1, Apr. 2, 1990, pp. 1-13.
Winestock et al. "Synthesis and Properties of Certain Substituted Lumazines", J. Org. Chem. 1961, 26, 4456-4462.

* cited by examiner

*Primary Examiner* — Timothy R Rozof
(74) *Attorney, Agent, or Firm* — Mark S. Cohen; Pearl Cohen Zedek Latzer Baratz LLP

(57) ABSTRACT

The invention described herein pertains to substituted indenoisoquinoline compounds as described herein, wherein $R^A$, $R^D$, W, X and Y are defined herein, pharmaceutical compositions and formulations comprising the indenoisoquinoline compounds, their synthesis, and methods for their use in the treatment and/or prevention of cancer.

28 Claims, 1 Drawing Sheet

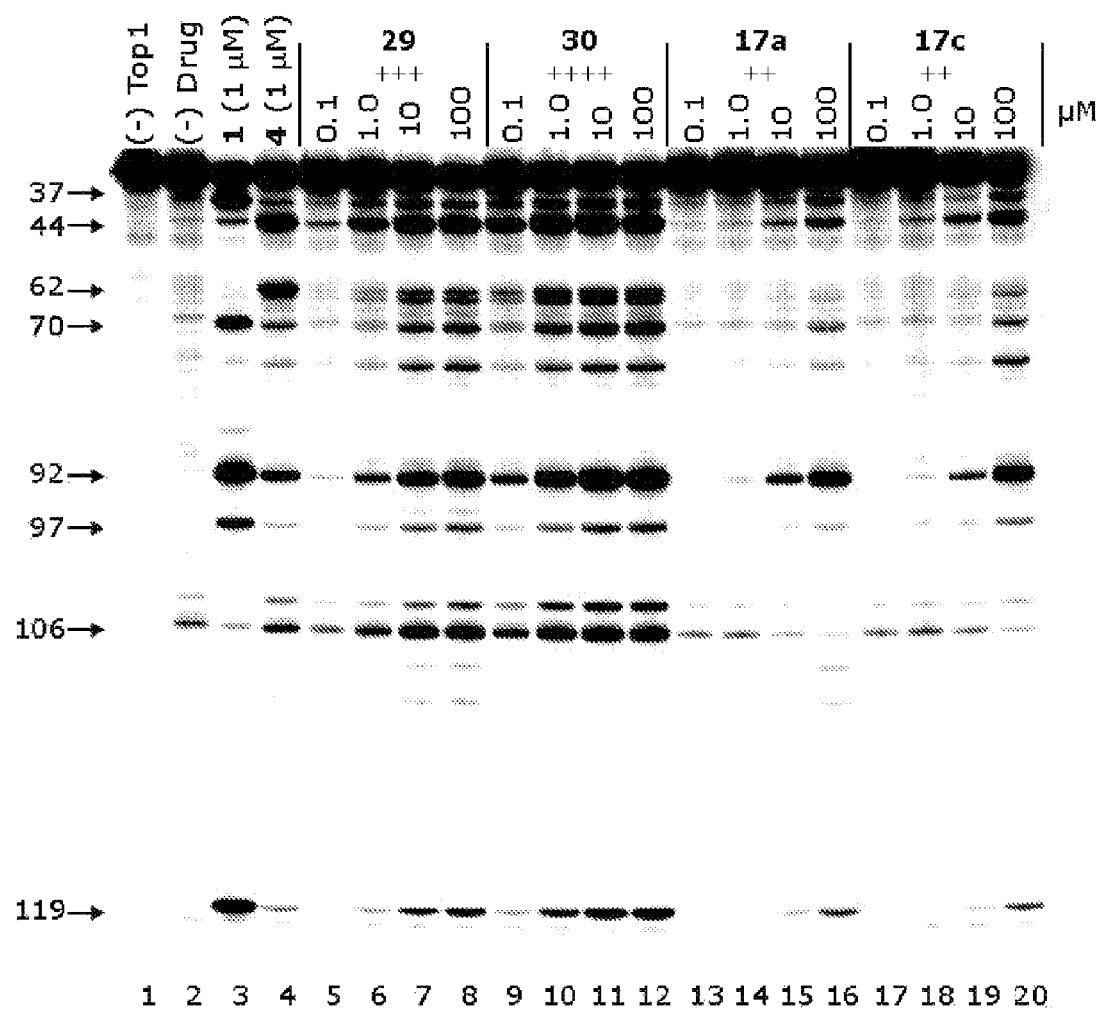

ALCOHOL-, DIOL-, AND CARBOHYDRATE-SUBSTITUTED INDENOISOQUINOLINES AS TOPOISOMERASE I INHIBITORS

CROSS REFERENCE TO RELATED APPLICATIONS

This application is a national stage entry under 35 USC §371(b) of International Application No. PCT/US2012/039365, filed May 24, 2012, and claims the benefit of U.S. Patent Application No. 61/489,900, filed May 25, 2011, the disclosures of both of which are hereby incorporated by reference in their entirety.

GOVERNMENT RIGHTS

This invention was made with government support under CA089566 awarded by the National Institutes of Health. The government has certain rights in the invention.

TECHNICAL FIELD

The invention described herein pertains to substituted indenoisoquinoline compounds, pharmaceutical compositions and formulations comprising the indenoisoquinoline compounds, their synthesis, and methods for their use in the treatment and/or prevention of cancer.

BACKGROUND AND SUMMARY OF THE INVENTION

Topoisomerase I (Top1) is an enzyme that is believed to relax supercoiled DNA. Relaxed DNA is reported to be required for many cellular processes such as DNA replication, transcription, and repair. Top1 is believed to relax DNA through a cycle of cleavage and religation steps involving the active site residue Tyr723. This residue is believed to attack the phosphodiester backbone, breaking the single strand and forming a covalent "cleavage complex" in which the unbroken strand undergoes "controlled rotation" and relaxes the DNA. After relaxation, the scissile strand is believed to be religated and the enzyme is released. As inhibition of Top1 is believed to be capable of leading to cell death, several Top1 inhibitors have been reportedly developed as a targeted approach for anti-cancer therapy. Camptothecin (1) and its clinically used analogues, topotecan (2) and irinotecan (3), were reported to inhibit Top1 activity by intercalating into the cleavage complex and preventing the religation step of the catalytic cycle. As a result, it is believed that advancing replication forks collide with the cleavage complex, resulting in double-stranded DNA breaks and apoptosis. Compounds that inhibit the religation reaction are commonly known as "Top1 poisons".

Representative Top1 Poisons.

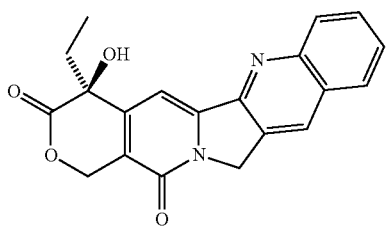

Camptothecin

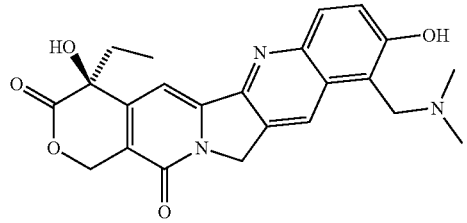

Topotecan

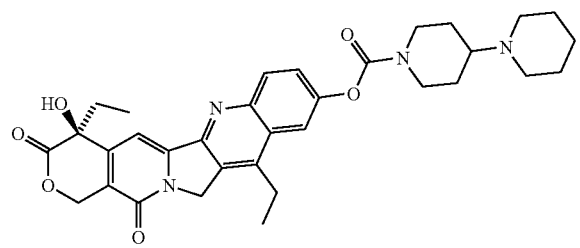

Irinotecan

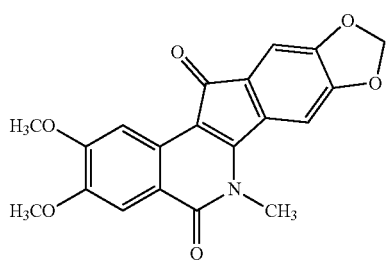

Although these inhibitors are reported to possess potent antitumor activity, issues regarding solubility and bioactivity, dose-limiting toxicity, and importantly, the instability of the hydroxy lactone and associated pharmacokinetic liabilities, have reportedly led to the development of therapeutic alternatives. A COMPARE analysis[Paull, K. D. et al., J. Natl. Cancer Inst. 1989, 81, 1088-1092] performed on the cytotoxicity profile of synthetic indenoisoquinoline 4 has been reported as showing many similarities to the cytotoxicity profile of camptothecin, indicating that compound 4 may exert its action through inhibition of Top1. [Pommier, Y. and Cushman, M., Mol. Cancer Ther. 2009, 8, 1008-1014.] Indeed, indenoisoquinolines such as 4 are believed to inhibit the religation reaction by an intercalative mechanism like camptothecin. Additionally, indenoisoquinolines are believed to be chemically stable, and many compounds in this class are believed to possess high antiproliferative activity.

It has been discovered herein that indenoisoquinolines can be modified to include branched or cyclic alkanols, or a hydroxy prodrugs thereof, and that the modified indenoisoquinolines are potent modulators of Top1 activity. Without being bound by theory, it is believed herein that indenoisoquinolines described herein form additional hydrogen bonds with residues available in the ternary complex. A comparison of crystal structures of Top1 ternary complexes is believed to reveal that branched or cyclic alkanols extend further out into the DNA major groove region. The aromatic core of the compounds appears to face Arg364 (with which they likely interact). The side chain appears to sit in close proximity to Asn352 and occupy similar spatial areas, where, accounting for flexibility, it is believed it may hydrogen bond with this residue, water, or flanking base pairs.

In one embodiment, described herein are the design, synthesis, and evaluation of indenoisoquinolines containing an N-branched or cyclic alkanol substituent, or a hydroxy prodrug thereof. In another illustrative embodiment, the indenoisoquinolines herein include compounds substituted with amines derived from aldohexoses and aldopentoses. In another illustrative embodiment, the indenoisoquinolines herein include compounds bearing shorter chiral side chains.

In another embodiment, described herein are compounds and compositions comprising series of alcohol, diol, and carbohydrate-substituted indenoisoquinolines. In another embodiment, described herein are the syntheses of these series of alcohol, diol, and carbohydrate-substituted indenoisoquinolines. In another embodiment, described herein are biological evaluations of these series of alcohol, diol, and carbohydrate-substituted indenoisoquinolines. In another embodiment, compounds described herein, including aldopentose and aldohexose-derived indenoisoquinolines, show activity across a panel of cancer cell lines. In another embodiment, compounds described herein show potent Top1 inhibitory activity when compared to camptothecin. In another embodiment, several of the compounds herein display potent Top1 poisoning and antiproliferative activities.

In another embodiment, indenoisoquinolines substituted with three-carbon alcohols and diols are described herein. In another embodiment, these three-carbon alcohol and diol-derived indenoisoquinolines appear to demonstrate activity across a panel of cancer cell lines. In another embodiment, several of these compounds appear to display potent Top1 inhibitory activity.

In one aspect of the Top1 inhibitory activity of the compounds herein, a stereochemical effect is observed.

In another embodiment, it is demonstrated herein that the activity of the indenoisoquinolines herein can be increased by ring substitution and by replacement of a primary alcohol with an amino group.

In another embodiment, pharmaceutical compositions containing one or more of the compounds are also described herein. In one aspect, the compositions include a therapeutically effective amount of the one or more compounds for treating a patient with cancer. It is to be understood that the compositions may include other components and/or ingredients, including, but not limited to, other therapeutically active compounds, and/or one or more carriers, diluents, excipients, and the like. In another embodiment, methods for using the compounds and pharmaceutical compositions for treating patients with cancer are also described herein. In one aspect, the methods include the step of administering one or more of the compounds and/or compositions described herein to a patient with cancer. In another aspect, the methods include administering a therapeutically effective amount of the one or more compounds and/or compositions described herein for treating patients with cancer. In another embodiment, uses of the compounds and compositions in the manufacture of a medicament for treating patients with cancer are also described herein. In one aspect, the medicaments include a therapeutically effective amount of the one or more compounds and/or compositions for treating a patient with cancer.

BRIEF DESCRIPTION OF THE DRAWINGS

FIG. 1 shows Top1-mediated DNA cleavage induced by indenoisoquinolines 29, 30, 17a, and 17c. Lane 1: DNA alone; lane 2: DNA plus Top1; lanes 3-20: DNA plus Top1 and indenoisoquinolines as indicated above gel. Numbers and arrows on the left indicate cleavage site positions.

DETAILED DESCRIPTION

It has been discovered herein that substituted indenoisoquinoline compounds and pharmaceutical compositions and formulations comprising these compounds are useful in the treatment and/or prevention of cancer.

In one embodiment, described herein is a compound of the formula

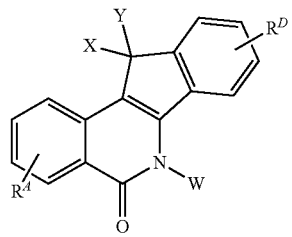

or a pharmaceutically acceptable salt thereof, wherein $R^A$ represents four substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^A$ represents at least two adjacent substituents that are taken together with the attached carbons to form an optionally substituted heterocycle; $R^D$ represents three substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^D$ represents at least two adjacent substituents that are taken together with the attached carbons to form an optionally substituted heterocycle; X and Y are each independently selected from the group consisting of hydrogen, and hydroxy, amino, hydroxylamino, and hydrazino, and derivatives thereof, and alkyl, heteroalkyl, cycloalkyl, cycloheteroalkyl, aryl, and arylalkyl, each of which is optionally substituted; or X and Y are taken together with the attached carbon to form carbonyl, imino, oximino, hydrazono, and alkylidenyl, each of which is optionally substituted; and W is a branched or cyclic alkanol, or a hydroxy prodrug thereof.

In another embodiment, described herein is the compound of any one of the preceding embodiments wherein hydroxy, or a derivative thereof is OH, alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, acyloxy or carbamate, each of which is optionally substituted.

In another embodiment, described herein is the compound of any one of the preceding embodiments wherein amino, or a derivative thereof is $NH_2$, alkylamino, and dialkylamino, where the two alkyl groups in dialkylamino may be the same or different, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, or acylamino, each of which is optionally substituted.

In another embodiment, described herein is the compound of any one of the preceding embodiments wherein thio, or a derivative thereof is SH, alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, acylthio, or thiocarbamate, each of which is optionally substituted.

In another embodiment, described herein is the compound as in the preceding embodiment wherein W is a polyhydroxyalkane.

In another embodiment, described herein is the compound as in any of the preceding embodiments wherein W is a diol.

In another embodiment, described herein is the compound as in any of the preceding embodiments wherein W is a carbohydrate.

In another embodiment, described herein is the compound as in any of the preceding embodiments wherein W is a sugar alcohol.

In another embodiment, described herein is the compound in any of the preceding embodiments wherein W contains less than 20 carbons.

In another embodiment, described herein is the compound in any of the preceding embodiments wherein W contains less than 10 carbons.

In another embodiment, described herein is the compound as in any of the preceding embodiments wherein W is a $C_3$-$C_6$ sugar alcohol.

In another embodiment, described herein is the compound as in any of the preceding embodiments wherein W is a $C_4$-$C_6$ sugar alcohol.

In another embodiment, described herein is the compound as in any of the preceding embodiments wherein W is a $C_5$-$C_6$ sugar alcohol.

In another embodiment, described herein is the compound as in any of the preceding embodiments wherein W includes a secondary or tertiary alcohol.

In another embodiment, described herein is the compound as in any of the preceding embodiments wherein W includes a secondary alcohol.

In another embodiment, described herein is the compound as in any of the preceding embodiments wherein W includes a branched alkyl.

In another embodiment, described herein is the compound as in any of the preceding embodiments wherein W is $CH_2CH$(OH)—R, where R is alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, or arylalkynyl, each of which is optionally substituted.

In another embodiment, described herein is the compound as in any of the preceding embodiments wherein W is $CH_2CH$(OH)—R, where R is alkyl, heteroalkyl, cycloalkyl, cycloheteroalkyl, carbaryl, carbarylalkyl, heteroaryl, or heteroarylalkyl, each of which is optionally substituted.

In another embodiment, described herein is the compound as in any of the preceding embodiments wherein W is $CH_2CH$(OH)—CH(OH)—R, where R is hydrogen, alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, or arylalkynyl, each of which is optionally substituted.

In another embodiment, described herein is the compound as in any of the preceding embodiments wherein W is $CH_2CH$(OH)—CH(OH)—R, where R is hydrogen, alkyl, heteroalkyl, cycloalkyl, cycloheteroalkyl, carbaryl, carbarylalkyl, heteroaryl, or heteroarylalkyl, each of which is optionally substituted.

In another embodiment, described herein is the compound as in any of the preceding embodiments wherein W is a ketoalkanol.

In another embodiment, described herein is the compound as in any of the preceding embodiments wherein W further includes an amino group.

In another embodiment, compounds are described herein where W is of the formula

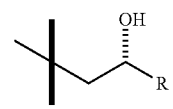

where R is alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, or arylalkynyl, each of which is optionally substituted. It has been observed herein that two indenoisoquinolines having propanediol substituents with different absolute stereochemistry showed differing anti-Top1 activity. The (S)-isomer 12a appears to possess higher Top1 inhibitory activity than the corresponding (R)-isomer 12b. The racemate 12c shows activity between that of the enantiopure forms.

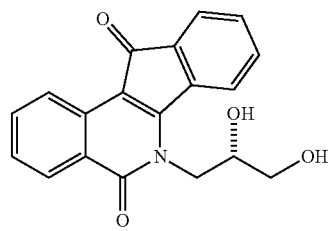

(S)-enantiomer 12a
Top1: +++

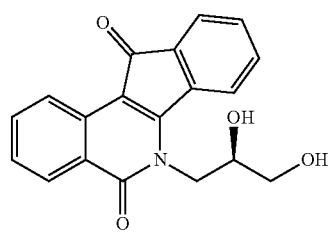

(R)-enantiomer 12b
Top1: 0/+

-continued

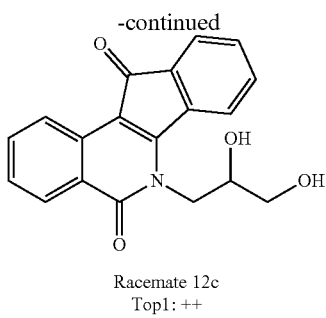

Racemate 12c
Top1: ++

Top1 inhibitory activity is expressed as relative to 1 μM camptothecin:
0, no measurable inhibitory activity;
+, between 20 and 50% activity;
++, between 50 and 75% activity;
+++, between 75% and 95% activity;
++++, equipotent;
0/+ indicates inhibition between 0 and +.

In another embodiment, described herein is a compound of the formula

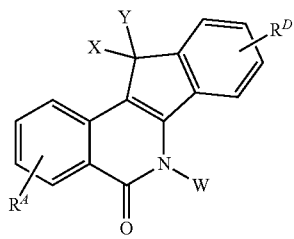

or a pharmaceutically acceptable salt thereof, wherein $R^A$ represents four substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^A$ represents at least two adjacent substituents that are taken together with the attached carbons to form an optionally substituted heterocycle; $R^D$ represents three substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^D$ represents at least two adjacent substituents that are taken together with the attached carbons to form an optionally substituted heterocycle; X and Y are each independently selected from the group consisting of hydrogen, and hydroxy, amino, hydroxylamino, and hydrazino, and derivatives thereof, and alkyl, heteroalkyl, cycloalkyl, cycloheteroalkyl, aryl, and arylalkyl, each of which is optionally substituted; or X and Y are taken together with the attached carbon to form carbonyl, imino, oximino, hydrazono, and alkylidenyl, each of which is optionally substituted; and W is a ketone or a prodrug thereof.

In another embodiment, described herein is the compound as in any of the preceding embodiments wherein W is a hydroxy ketone.

In another embodiment, described herein is the compound as in any of the preceding embodiments wherein W is a hydrogen bond forming group.

In another embodiment, described herein is the compound as in any of the preceding embodiments wherein W is capable of forming one or more hydrogen bonds with residues in the DNA major groove.

In another embodiment, described herein is the compound as in any of the preceding embodiments wherein W is capable of forming a hydrogen bond with Asn352 of a topoisomerase I.

In another embodiment, described herein is the compound as in any of the preceding embodiments wherein $R^A$ represents four substituents each independently selected from the group consisting of hydrogen, halo, and nitro, and hydroxy, amino, and thio, and derivatives thereof, and acyl, sulfoxyl, and sulfonyl, and $CO_2H$, and $SO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted; or $R^A$ represents at least two adjacent substituents that are taken together with the attached carbons to form an optionally substituted heterocycle.

In another embodiment, described herein is the compound as in any of the preceding embodiments wherein $R^A$ represents four substituents each independently selected from the group consisting of hydrogen, halo, and nitro, and hydroxy, amino, and thio, and derivatives thereof, and acyl, sulfoxyl, and sulfonyl, and $CO_2H$, and $SO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted.

In another embodiment, described herein is the compound as in any of the preceding embodiments wherein $R^A$ represents four substituents each independently selected from the group consisting of halo, and nitro, and hydroxy, amino, and thio, and derivatives thereof, and acyl, sulfoxyl, and sulfonyl, and $CO_2H$, and $SO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted.

In another embodiment, described herein is the compound as in any of the preceding embodiments wherein $R^A$ represents four substituents each independently selected from the group consisting of hydrogen, halo, and nitro, and hydroxy, amino, and thio, and derivatives thereof, and acyl, sulfoxyl, and sulfonyl, and $CO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted.

In another embodiment, described herein is the compound as in any of the preceding embodiments wherein $R^A$ represents four substituents each independently selected from the group consisting of halo, and nitro, and hydroxy, amino, and thio, and derivatives thereof, and acyl, sulfoxyl, and sulfonyl, and $CO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted.

In another embodiment, described herein is the compound as in any of the preceding embodiments wherein $R^A$ represents two adjacent substituents that are taken together with the attached carbons to form an optionally substituted heterocycle.

In another embodiment, described herein is the compound as in any of the preceding embodiments wherein $R^D$ represents four substituents each independently selected from the group consisting of hydrogen, halo, and nitro, and hydroxy, amino, and thio, and derivatives thereof, and acyl, sulfoxyl, and sulfonyl, and $CO_2H$, and $SO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted; or $R^D$ represents at least two adjacent substituents that are taken together with the attached carbons to form an optionally substituted heterocycle.

In another embodiment, described herein is the compound as in any of the preceding embodiments wherein $R^D$ represents four substituents each independently selected from the group consisting of hydrogen, halo, and nitro, and hydroxy, amino, and thio, and derivatives thereof, and acyl, sulfoxyl, and sulfonyl, and $CO_2H$, and $SO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted.

In another embodiment, described herein is the compound as in any of the preceding embodiments wherein $R^D$ represents four substituents each independently selected from the group consisting of, halo and nitro, and hydroxy, amino, and thio, and derivatives thereof, and acyl, sulfoxyl, and sulfonyl, and $CO_2H$, and $SO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted.

In another embodiment, described herein is the compound as in any of the preceding embodiments wherein $R^D$ represents four substituents each independently selected from the group consisting of, halo, and nitro, and hydroxy, amino, and thio, and derivatives thereof, and acyl, sulfoxyl, and sulfonyl, and $CO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted.

In another embodiment, described herein is the compound as in any of the preceding embodiments wherein $R^D$ represents two adjacent substituents that are taken together with the attached carbons to form an optionally substituted heterocycle.

In another embodiment, described herein is the compound as in any of the preceding embodiments wherein at least one of $R^A$ is nitro.

In another embodiment, described herein is the compound as in any of the preceding embodiments wherein at least one of $R^A$ is alkoxy.

In another embodiment, described herein is the compound as in any of the preceding embodiments wherein at least one of $R^A$ is methoxy.

In another embodiment, described herein is the compound as in any of the preceding embodiments wherein at least two of $R^A$ are bismethoxy.

In another embodiment, described herein is the compound as in any of the preceding embodiments wherein at least two of $R^A$ are alkylenedioxy.

In another embodiment, described herein is the compound as in any of the preceding embodiments wherein at least two of $R^A$ are methylenedioxy.

In another embodiment, described herein is the compound as in any of the preceding embodiments wherein at least one of $R^D$ is nitro.

In another embodiment, described herein is the compound as in any of the preceding embodiments wherein at least one of $R^D$ is alkoxy.

In another embodiment, described herein is the compound as in any of the preceding embodiments wherein at least one of $R^D$ is methoxy.

In another embodiment, described herein is the compound as in any of the preceding embodiments wherein at least two of $R^D$ are bismethoxy.

In another embodiment, described herein is the compound as in any of the preceding embodiments wherein at least two of $R^D$ are alkylenedioxy.

In another embodiment, described herein is the compound as in any of the preceding embodiments wherein at least two of $R^D$ are methylenedioxy.

In another embodiment, described herein is the compound as in any of the preceding embodiments wherein X and Y are taken together with the attached carbon to form carbonyl.

In another embodiment, described herein is a compound of the formula

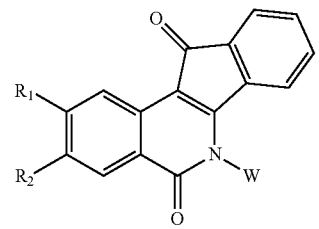

or a pharmaceutically acceptable salt thereof, wherein
$R_1$ is hydrogen or methoxy;
$R_2$ is hydrogen, methoxy, or nitro; and
W is selected from the group consisting of

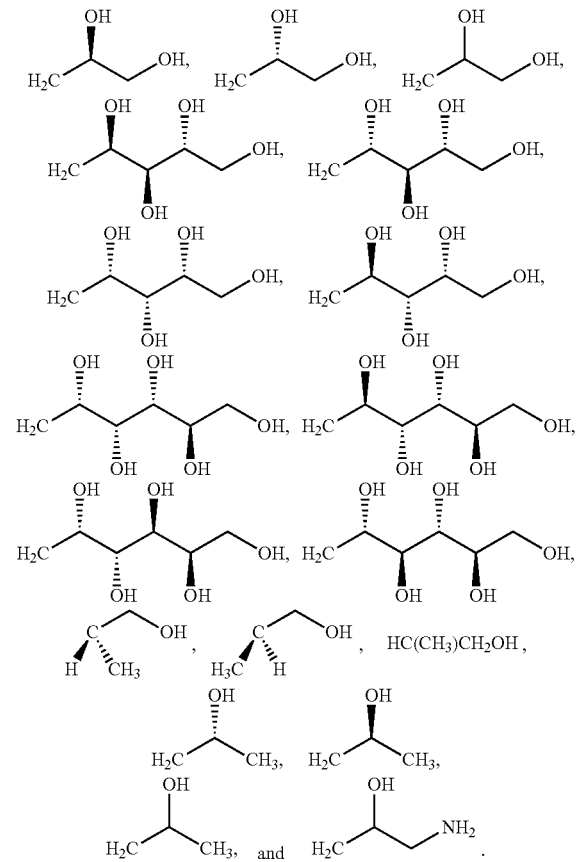

Several illustrative embodiments of the invention are described by the following enumerated clauses:

1. A compound of the formula

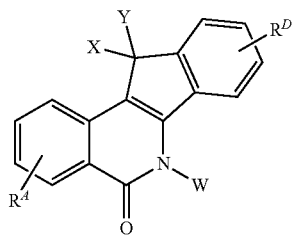

or a pharmaceutically acceptable salt thereof, wherein $R^A$ represents four substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^A$ represents at least two adjacent substituents that are taken together with the attached carbons to form an optionally substituted heterocycle;

$R^D$ represents three substituents each independently selected from the group consisting of hydrogen, halo, azido, and nitro, and hydroxy, amino, and thio, and derivatives thereof, and acyl, sulfoxyl, sulfonyl, phosphinyl, and phosphonyl, and $CO_2H$, $SO_2H$, $SO_3H$, $PO_2H$, and $PO_3H$, and derivatives thereof, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^D$ represents at least two adjacent substituents that are taken together with the attached carbons to form an optionally substituted heterocycle;

X and Y are each independently selected from the group consisting of hydrogen, and hydroxy, amino, hydroxylamino, and hydrazino, and derivatives thereof, and alkyl, heteroalkyl, cycloalkyl, cycloheteroalkyl, aryl, and arylalkyl, each of which is optionally substituted; or X and Y are taken together with the attached carbon to form carbonyl, imino, oximino, hydrazono, and alkylidenyl, each of which is optionally substituted; and W is a branched or cyclic alkanol, or a hydroxy prodrug thereof, or W is a ketone or a prodrug thereof. 1a. The compound as in clause 1 wherein W is a branched or cyclic alkanol, or a hydroxy prodrug thereof. 2. The compound as in clause 1 wherein W is a polyhydroxyalkane. 3. The compound as in any one of the preceding clauses wherein W is an diol. 4. The compound as in any one of the preceding clauses wherein W is a carbohydrate. 5. The compound as in any one of the preceding clauses wherein W is a sugar alcohol. 6. The compound as in any one of the preceding clauses wherein W is a $C_3$-$C_6$ sugar alcohol. 7. The compound as in any one of the preceding clauses wherein W is a $C_4$-$C_6$ sugar alcohol. 8. The compound as in any one of the preceding clauses wherein W is a $C_5$-$C_6$ sugar alcohol. 9. The compound as in any one of the preceding clauses wherein W includes a secondary or tertiary alcohol. 10. The compound as in any one of the preceding clauses wherein W includes a secondary alcohol. 11. The compound as in any one of the preceding clauses wherein W includes a branched alkyl. 12. The compound as in any one of the preceding clauses wherein W is $CH_2CH(OH)$—R, where R is alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, or arylalkynyl, each of which is optionally substituted. 13. The compound as in any one of the preceding clauses wherein W is $CH_2CH(OH)$—R, where R is alkyl, heteroalkyl, cycloalkyl, cycloheteroalkyl, carbaryl, carbarylalkyl, heteroaryl, or heteroarylalkyl, each of which is optionally substituted. 14. The compound as in any one of the preceding clauses wherein W is $CH_2CH(OH)$—$CH(OH)$—R, where R is hydrogen, alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, or arylalkynyl, each of which is optionally substituted. 15. The compound as in any one of the preceding clauses wherein W is $CH_2CH(OH)$—$CH(OH)$—R, where R is hydrogen, alkyl, heteroalkyl, cycloalkyl, cycloheteroalkyl, carbaryl, carbarylalkyl, heteroaryl, or heteroarylalkyl, each of which is optionally substituted. 16. The compound as in any one of the preceding clauses wherein W is a ketoalkanol. 17. The compound as in any one of the preceding clauses wherein W includes an amino group. 18. The compound as in any one of the preceding clauses wherein W includes the following divalent radical

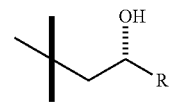

where R is alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, or arylalkynyl, each of which is optionally substituted. 19. The compound as in clause 1 wherein W is a ketone or a prodrug thereof. 20. The compound as in the preceding clause wherein W is a hydroxy ketone. 21. The compound as in any one of the preceding clauses wherein W is a hydrogen bond forming group. 22. The compound as in any one of the preceding clauses wherein W is capable of forming one or more hydrogen bonds with residues in the DNA major groove. 23. The compound as in any one of the preceding clauses wherein W is capable of forming a hydrogen bond with Asn352 of a topoisomerase I. 24. The compound as in any one of the preceding clauses wherein $R^A$ represents four substituents each independently selected from the group consisting of hydrogen, halo, and nitro, and hydroxy, amino, and thio, and derivatives thereof, and acyl, sulfoxyl, and sulfonyl, and $CO_2H$, and $SO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted; or $R^A$ represents at least two adjacent substituents that are taken together with the attached carbons to form an optionally substituted heterocycle. 25. The compound as in any one of the preceding clauses wherein $R^A$ represents four substituents each independently selected from the group consisting of, halo, and nitro, and hydroxy, amino, and thio, and derivatives thereof, and acyl, sulfoxyl, and sulfonyl, and $CO_2H$, and $SO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted. 26. The compound as in any one of the preceding clauses wherein $R^A$ represents four substituents each independently selected from the group consisting of, halo, and nitro, and hydroxy, amino, and thio, and derivatives thereof, and acyl, sulfoxyl, and sulfonyl, and $CO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted. 27. The compound as in any one of the preceding clauses wherein $R^A$ represents two adjacent substituents that are taken together with the attached carbons to form an optionally substituted heterocycle. 28. The compound as in any one of the preceding clauses wherein $R^D$ represents four substituents each independently selected from the group consisting of hydrogen, halo, and nitro, and hydroxy, amino, and thio, and derivatives thereof, and acyl, sulfoxyl, and sulfonyl, and $CO_2H$, and $SO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted; or $R^D$ represents at least two adjacent substituents that are taken together with the attached carbons to form an optionally substituted heterocycle. 29. The compound as in any one of the preceding clauses wherein $R^D$ represents four substituents each independently selected from the group consisting of, halo, and nitro, and hydroxy, amino, and thio, and derivatives thereof, and acyl, sulfoxyl, and sulfonyl, and $CO_2H$, and $SO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted. 30. The compound as in any one of the preceding clauses wherein $R^D$ represents four substituents each independently selected from the group consisting of, halo, and nitro, and hydroxy, amino, and thio, and derivatives thereof, and acyl, sulfoxyl, and sulfonyl, and $CO_2H$, and derivatives thereof, and alkyl, heteroalkyl, cycloalkyl, cycloheteroalkyl, carbaryl, carbarylalkyl, heteroaryl, and heteroarylalkyl, each of which is optionally substituted. 31. The compound as in any one of the preceding clauses wherein $R^D$ represents two adjacent substituents that are taken together with the attached carbons to form an optionally substituted heterocycle. 32. The compound as in any one of the preceding clauses wherein at least one of $R^A$ is nitro. 33. The compound as in any one of the preceding clauses wherein at least one of $R^A$ is alkoxy. 34. The compound as in any one of the preceding clauses wherein at least one of $R^A$ is methoxy. 35. The compound as in any one of the preceding clauses wherein at least two of $R^A$ are bismethoxy. 36. The compound as in any one of the preceding clauses wherein at least two of $R^A$ are alkylenedioxy. 37. The compound as in any one of the preceding clauses wherein at least two of $R^A$ are methylenedioxy. 38. The compound as in any one of the preceding clauses wherein at least one of $R^D$ is nitro. 39. The compound as in any one of the preceding clauses wherein at least one of $R^D$ is alkoxy. 40. The compound as in any one of the preceding clauses wherein at least one of $R^D$ is methoxy. 41. The compound as in any one of the preceding clauses wherein at least two of $R^D$ are bismethoxy. 42. The compound as in any one of the preceding clauses wherein at least two of $R^D$ are alkylenedioxy. 43. The compound as in any one of the preceding clauses wherein at least two of $R^D$ are methylenedioxy. 44. The compound as in any one of the preceding clauses wherein X and Y are taken together with the attached carbon to form carbonyl. 45. A pharmaceutical composition comprising one or more compounds of any one of the preceding clauses for treating cancer. 46. A unit dose or unit dosage form composition comprising a therapeutically effective amount of one or more compounds of any one of the preceding clauses for treating cancer. 47. The composition or unit dose or unit dosage form of clause 45 or clause 46 further comprising one or more carriers, diluents, or excipients, or a combination thereof. 48. A method for treating cancer, the method comprising the step of administering to a patient in need of relief from the cancer a composition comprising a therapeutically effective amount of one or more compounds of any one of the preceding clauses. 49. The method of clause 48 wherein the composition further comprises one or more carriers, diluents, or excipients, or a combination thereof. 50. Use of one or more compounds of any one of the preceding clauses in the manufacture of a medicament for treating cancer. 51. A process for preparing a compound of clause 1, the process comprising the step of contacting

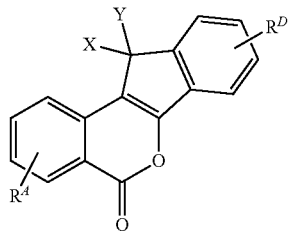

with $H_2N$—W, where W is a branched or cyclic alkanol, and where the hydroxy is not protected.

In another embodiment, described herein is a pharmaceutical composition comprising one or more of the compounds described in any one of the preceding embodiments, and optionally one or more carriers, diluents, or excipients, or a combination thereof.

In another embodiment, described herein is a pharmaceutical composition comprising one or more compounds of any one of the preceding embodiments for treating cancer.

In another embodiment, described herein is a unit dose or unit dosage form composition comprising a therapeutically effective amount of one or more compounds of any one of the preceding embodiments for treating cancer.

In another embodiment, described herein is the composition or unit dose or unit dosage form as in the preceding embodiment further comprising one or more carriers, diluents, or excipients, or a combination thereof.

In another embodiment, described herein is a method for treating cancer, the method comprising the step of administering to a patient in need of relief from the cancer a composition comprising a therapeutically effective amount of one or more compounds of any one of the preceding embodiments.

In another embodiment, described herein is the method of the preceding embodiment wherein the composition further comprises one or more carriers, diluents, or excipients, or a combination thereof.

In another embodiment, described herein is the use of one or more compounds of any one of the preceding embodiments in the manufacture of a medicament for treating cancer.

In another embodiment, described herein is the use of one or more compounds of any one of the embodiments described herein for the treatment of cancer.

In another embodiment, described herein is a process for preparing the compound of any one of the preceding embodiments, the process comprising the step of contacting

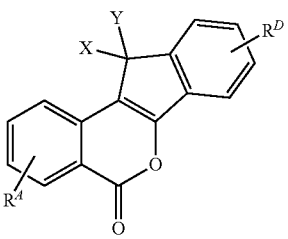

with H₂N—W, where W is a branched or cyclic alkanol, and where the hydroxy is not protected.

In another embodiment, described herein is a process for preparing the compound of any one of the preceding embodiments, the process comprising the step as shown in the following scheme:

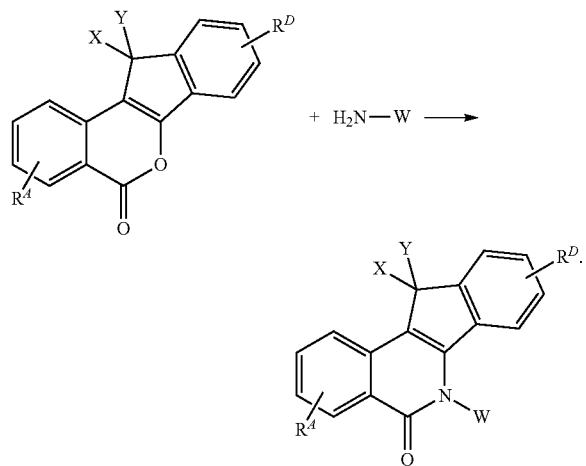

In another embodiment, described herein is a method for treating a disease responsive to inhibition of topoisomerase 1, the method comprising the step of administering one or more of the compounds or the compositions described herein to a patient having the disease. In one embodiment, the disease is a cancer. In another embodiment, the cancer is ovarian cancer, small-cell lung cancer, cervical cancer, colon cancer or rectal cancer.

It is to be understood that, as used herein, the term "indenoisoquinoline", as well as the various embodiments represented by the formulae described herein, generally refers to the parent compounds as well as pharmaceutically acceptable salts thereof, including acid and/or base addition salts. In addition, the term and representative formulae include hydrates and solvates thereof. In addition, the term and representative formulae include all morphological forms of the compound, including amorphous forms as well as any particular crystal morphology or mixture thereof. In addition, it is to be understood that various prodrugs of the compounds are described herein.

In another embodiment, described herein are pharmaceutical compositions comprising one or more of the substituted indenoisoquinolines. The substituted indenoisoquinolines and the pharmaceutical compositions comprising them are useful in the treatment of diseases such as cancer.

In another embodiment, described herein are methods of use of the substituted indenoisoquinolines and the pharmaceutical compositions comprising them for treating diseases such as cancer. Illustratively, these methods include administering to a patient in need of relief from the disease a therapeutically effective amount of one or more of the substituted indenoisoquinolines and/or the pharmaceutical compositions comprising them. In one aspect, the methods described herein include co-therapies with other therapeutic agents known in the art. Accordingly, the compounds, compositions, formulations and methods described herein may be combined with any one or more of the known compounds or agents known in the art. Accordingly, the co-therapy includes the co-administration of one or more of the compounds described herein and one or more of the known compounds or agents known in the art.

It is to be understood that in each of the embodiments described herein, the physical state of the compounds may be amorphous, or in any of a variety of morphological forms. In addition, it is to be understood that the compounds described herein may each be included in the compositions and methods described herein as any number of a variety of pharmaceutical salt forms, or as a hydrate or other solvate.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that alkyl is advantageously of limited length, including $C_1$-$C_{24}$, $C_1$-$C_{12}$, $C_1$-$C_8$, $C_1$-$C_6$, and $C_1$-$C_4$. It is to be further understood that alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior.

As used herein, the term "cycloalkyl" includes a chain of carbon atoms, which is optionally branched, where at least a portion of the chain is cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic groups, including aromatic carbocyclic and aromatic heterocyclic groups, each of which may be optionally substituted. As used herein, the term "carbaryl" includes aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, acyloxy, and the like, each of which is optionally substituted. It is appreciated that the term "alkoxy" can be used interchangeably with term "alkyloxy." The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, acylcarbonyl, and the like, each of which is optionally substituted.

As used herein, the term "sulfoxyl" (also known as "sulfinyl") includes alkylS(O), alkenylS(O), alkynylS(O), heteroalkylS(O), heteroalkenylS(O), heteroalkynylS(O), cycloalkylS(O), cycloalkenylS(O), cycloheteroalkylS(O), cycloheteroalkenylS(O), arylS(O), arylalkylS(O), arylalkenylS(O), arylalkynylS(O), and the like, each of which is optionally substituted. Illustrative examples of sulfoxyl include MeS(O), EtS(O), PrS(O), i-PrS(O), t-BuS(O), PhS(O), and the like.

As used herein, the term "carboxylate and derivatives thereof" includes the group $CO_2H$ and salts thereof, and esters and amides thereof, and CN.

As used herein, the term "sulfinyl or a derivative thereof" includes $SO_2H$ and salts thereof, and esters and amides thereof.

As used herein, the term "sulfonyl or a derivative thereof" includes $SO_3H$ and salts thereof, and esters and amides thereof.

As used herein, the term "phosphinyl or a derivative thereof" includes $P(R)O_2H$ and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl (carbaryl+heteroaryl), or arylalkyl, each of which is optionally substituted.

As used herein, the term "phosphonyl or a derivative thereof" includes $PO_3H_2$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH acyloxy, and the like, each of which is optionally substituted.

As used herein, the term "hydrazino and derivatives thereof" includes alkylNHNH, alkenylNHNH, alkynylNHNH, heteroalkylNHNH, heteroalkenylNHNH, heteroalkynylNHNH, cycloalkylNHNH, cycloalkenylNHNH, cycloheteroalkylNHNH, cycloheteroalkenylNHNH, arylNHNH, arylalkylNHNH, arylalkenylNHNH, arylalkynylNHNH, acylNHNH, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like.

Illustrative substituents include, but are not limited to, a radical $—(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from $—CO_2R^4$ and $—CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$) alkoxy, each of which is optionally further substituted with one or more of 1 to 3 halogen atoms; optionally substituted aryl($C_2$-$C_{16}$)alkanoyl, such as the aryl radical being unsubstituted or substituted by 1 to 3 substituents selected from the group consisting of halogen, ($C_1$-$C_3$)alkyl and ($C_1$-$C_3$) alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustratively, administering includes local use, such as when administered locally to the site of disease, injury, or defect. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

It is to be understood that in the methods described herein, the individual components of a co-administration or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration. Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that as used herein, the term "carbohydrate" includes a wide variety of radicals, including naturally occurring carbohydrates, and derivatives thereof, other radicals that include a C:O ratio of about 2 or less, or at least about 3 hydroxy groups, and the like. It is to be further understood that carbohydrates include reduced sugars, such as glycerol, erythritol, threitol, arabitol, xylitol, ribitol, mannitol, sorbitol, dulcitol, iditol, and the like. In addition, any of the foregoing illustrative examples of carbohydrates may also include other functional groups, including but not limited to carboxylic or sulfonic acids, ketones or aldehydes, or amines, or combinations of the foregoing.

In another embodiment, the compounds described herein are capable of forming hydrogen bonds, including forming one or more hydrogen bonds between W and residues in the DNA major groove, and/or hydrogen bonds between W and Asn352 of a topoisomerase I. One illustrative method for assessing the capability of a compound described herein for forming such a hydrogen bond is using molecular modeling as described herein. Illustrative molecular modeling is performed using GOLD, SYBYL, and the like.

In another embodiment, compounds of formula C are described wherein $R^A$ and $R^D$ are as described herein, and R is aryl, alkyl, cycloalkyl, cycloheteroalkyl, or heteroalkyl, each of which is optionally substituted. In another embodiment a process for preparing compounds of formula C is described (see Scheme A).

Scheme A

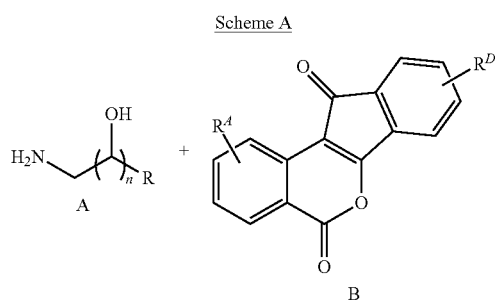

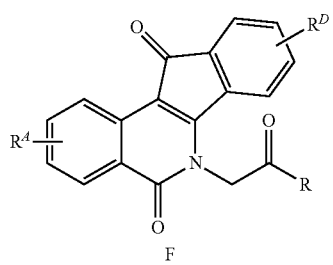

Reagents and conditions:
(a) CHCl₃, reflux;
(b) NMO, TPAP, CH$_2$Cl$_2$, r.t.

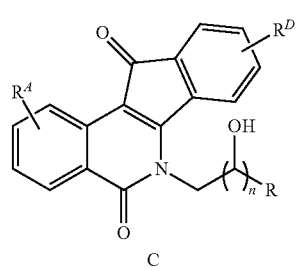

In another embodiment, compounds of formula F are described wherein $R^A$ and $R^D$ are as described herein, and R is aryl, alkyl, cycloalkyl, cycloheteroalkyl, or heteroalkyl, each of which is optionally substituted. In another embodiment a process for preparing compounds of formula F is described (see Scheme B).

Scheme B

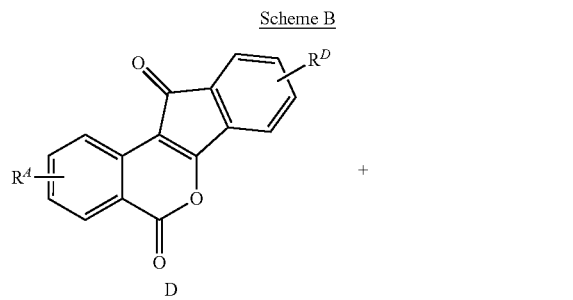

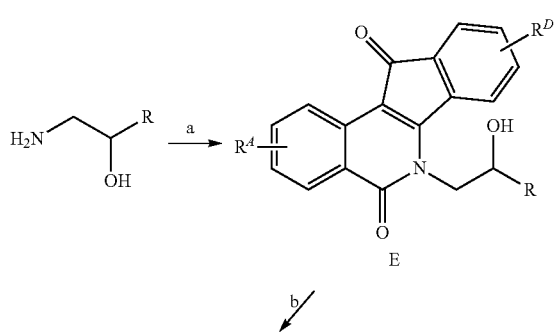

It is to be understood that hydrogen bonds described herein may be made directly between functional groups on compounds described herein and residues on DNA and/or TopI, or such hydrogen bonds described herein may be made indirectly between functional groups on compounds described herein and residues on DNA and/or TopI through an intervening solvent molecule, such as water.

EXAMPLES

The following examples further illustrate specific embodiments of the invention; however, the following examples should not be interpreted in any way to limit the invention.

Example

Chemistry. Aldopentose and Aldohexose Substituents. In a previous publication, the installation of indenoisoquinoline side chains involving condensation of the indenoisochromenone lactone (a vinylogous anhydride, e.g. compound 16, Scheme 1) with a primary amine was reported. The preparation of carbohydrate-derived indenoisoquinolines followed a similar approach, by the conversion of the aldose into an aminodeoxyalditol. Without being bound by theory, it was speculated that protection of the hydroxyl groups of the monosaccharide may be necessary to carry out the required transformations. However, the published method of Winestock and Plaut for preparation of aminodeoxyalditols was employed without recourse to protecting groups. [Winestock, C. H., et al., *J. Org. Chem.* 1961, 26, 4456-4462] This method is shown for D-arabinose (15a, Scheme 1) and proved successful for all sugars investigated.

Scheme 1

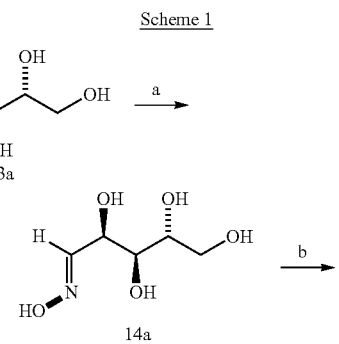

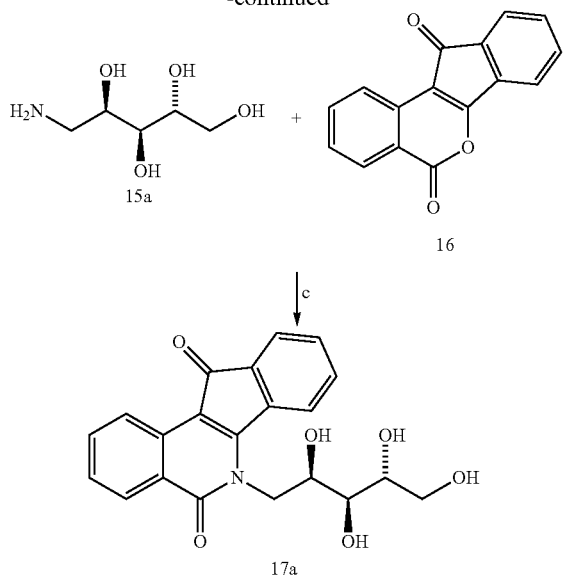

Reagents and conditions: (a) i. H₂NOH•HCl, NaOMe, EtOH, r.t. ii. 13a, 70° C; (b) PT(IV)O₂, H₂ (40 psi), AcOH, r.t; (c) MeOH or CHCl₃ (MeOH for example shown), reflux.

Example

D-Arabinose (13a) was treated with hydroxylamine hydrochloride in the presence of sodium methoxide to afford the corresponding oxime 14a as a mixture of (E)- and (Z)-diastereomers. [Finch, P., et al., *Journal of the Chemical Society-Perkin Transactions* 1 1975, 1682-1686; Snyder, J. R., *Carbohydr. Res.* 1990, 198, 1-13] The mixture was hydrogenated in the presence of catalytic Pt(IV)O₂ to afford D-arabitylamine (15a) in quantitative yield following ion-exchange chromatography. Likewise, D-ribose (13b), D-glucose (13c), D-xylose (13d), D-lyxose (13e), D-mannose (13f), D-galactose (13g) and D-allose (13h) were converted into their respective oximes (or diastereomeric mixtures of oximes) 14b-h (structures given in Table 1). These oximes were reduced to amines 15b-h, respectively. To prepare indenoisoquinolines, lactone 16 was condensed with excess aminodeoxyalditol in refluxing MeOH or CHCl₃ (also shown for arabinose in Scheme 1). The indenoisoquinolines 17a-h were obtained in moderate yields.

TABLE 1

Aldopentose and aldohexose-based substituents.

| Aldose | Oxime | Amine | Indenoisoquinoline R group |
|---|---|---|---|
| 13a | 14a | 15a | 17a |
| 13b | 14b | 15b | 17b |
| 13c | 14c | 15c | 17c |

TABLE 1-continued
Aldopentose and aldohexose-based substituents.
| Aldose | Oxime | Amine | Indenoisoquinoline R group |
|---|---|---|---|
| 13d | 14d | 15d | 17d |
| 13e | 14e | 15e | 17e |
| 13f | 14f | 15f | 17f |
| 13g | 14g | 15g | 17g |
| 13h | 14h | 15h | 17h |
Example 50
Indenoisoquinoline (19) was prepared from D-glucamine (15c) and the nitrated lactone 18, as shown in Scheme 2.
Scheme 2
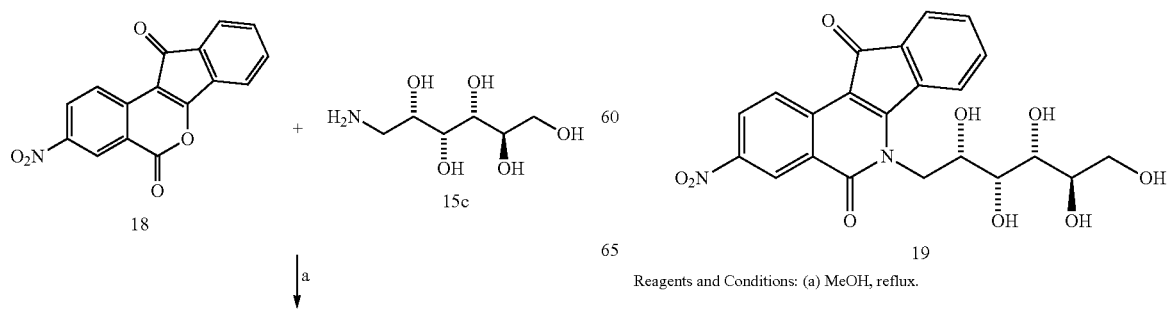
Reagents and Conditions: (a) MeOH, reflux.

Example

Three-Carbon Alcohol and Diol Substituents. Indenoisoquinolines 12a, 12b, and 12c were prepared by condensation of lactone 16 with commercially available aminoalcohols 20a, 20b, and 20c to afford the (S), (R), and racemic compounds, respectively (Scheme 3). As the stereochemistry of the 2'-hydroxyl group appeared to play a role in the inhibition of Top1 (FIG. 3) and there is no crystal structure of these compounds in ternary complex with DNA and Top1 available, additional compounds were synthesized in order to elucidate the function (and possible stereochemical SAR) of the 2' substituent. Without being bound by theory, it was hypothesized that the 2'-hydroxyl group may form a crucial hydrogen bond in the ternary complex. To test this hypothesis, the 2'-hydroxyl group was first replaced with a methyl group, abolishing the H-bonding potential at this position. The racemic amino alcohol 21c, along with the enantiopure alcohols 21a and 21b (all commercially available), were condensed with lactone 16 to give the corresponding indenoisoquinolines 22a-c (Scheme 3).

Example

Another compound, 25 (Scheme 4), possesses a 2'-keto group instead of the 2'-hydroxyl. It is appreciated that replacing a hydroxyl group with a keto group may switch that substituent's properties from H-bond donor/acceptor to solely H-bond acceptor. Attempts to selectively oxidize the 2'-hydroxyl of 12c were unsuccessful. Compound 25 was prepared by the approach depicted in Scheme 4. 1-Amino-2,3-propanediol (20c) was condensed with lactone 16 to yield the racemic indenoisoquinoline 12c. Selective protection of the primary alcohol (as the silyl ether 23) was followed by oxidation of the secondary alcohol using Ley's conditions [Ley, S. V., et al., *Synthesis* 1994, 639-666.] to yield indenoisoquinoline 24. Acidic cleavage of the protecting group afforded the ketone analogue 25.

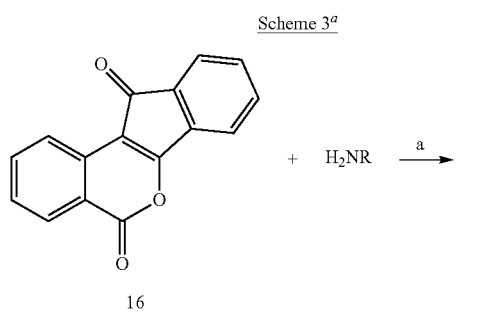

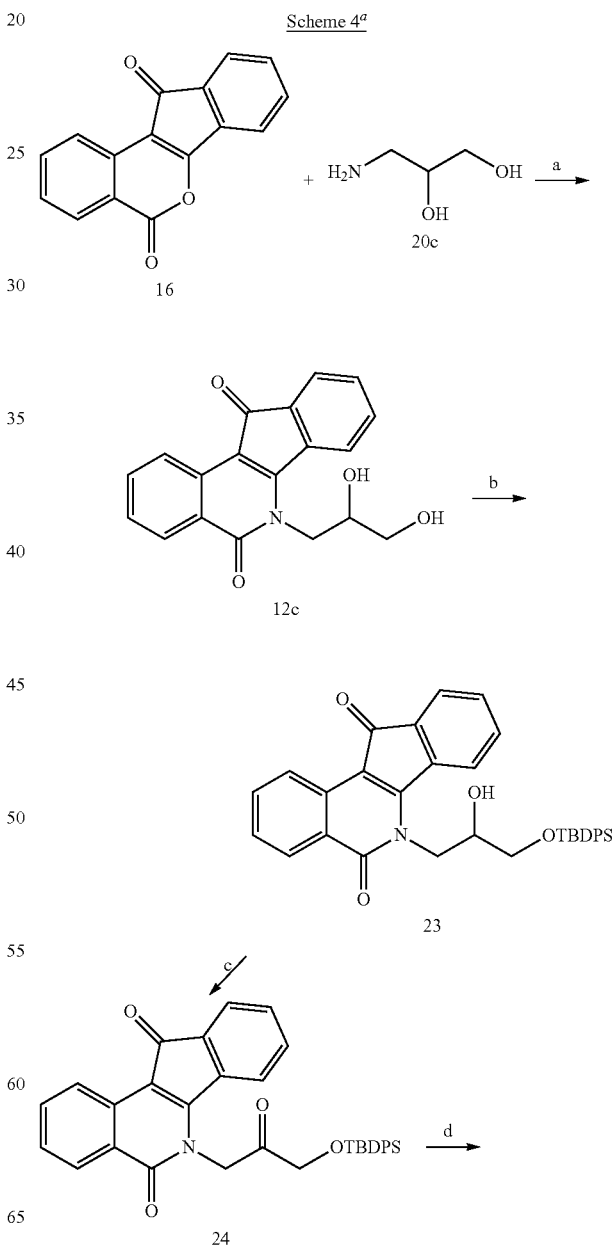

[a]Reagents and Conditions: (a) CHCl₃ or MeOH, reflux.

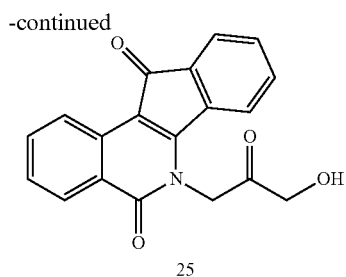

Reagents and conditions: (a) CHCl₃, reflux; (b) TBDPSCl, Et₃N, 4-DMAP, CH₂Cl₂; (c) NMO, TPAP, CH₂Cl₂, r.t.; (d) methanolic HCl, r.t.

Example

Scheme 5 depicts the synthesis of "truncated" diol indenoisoquinolines 27a-c and the amino analogue 27d. Lactone 16 was condensed with commercially available alcohols 26a-d to afford the respective indenoisoquinolines 27a-d. Compounds 27a-c do not include the 3' hydrogen-bonding group, whereas in compound 27d the hydroxyl group was replaced with an amino group.

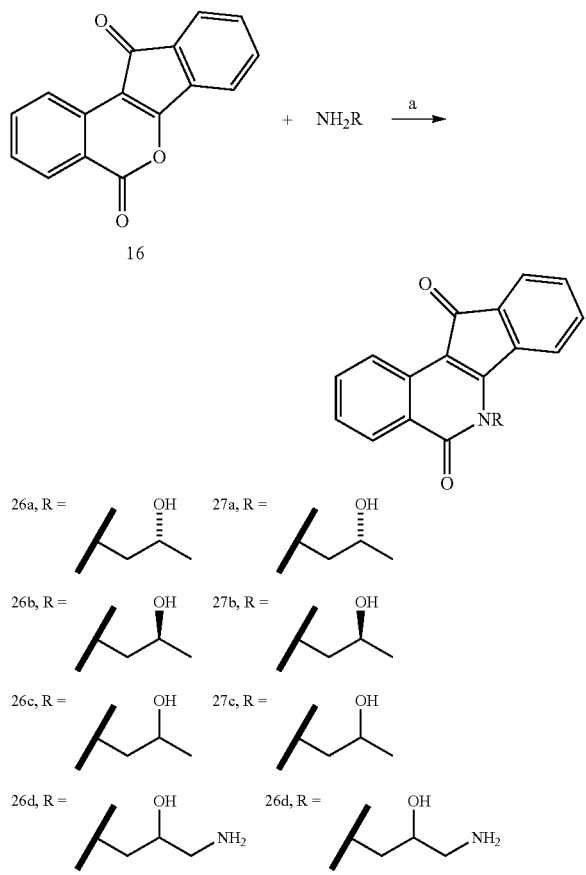

Reagents and conditions: (a) CHCl₃, reflux.

Additionally, two ring-substituted diol compounds were prepared using the same rationale for the synthesis of 19. Dimethoxy- and nitro-substituted lactones (28 and 18, respectively)[Morrell, A., et al., *Bioorg. Med. Chem. Lett.* 2004, 14, 3659-366; 3 Morrell, A., et al., *J. Med. Chem.* 2006, 49, 7740-7753] were condensed with (S)-diol 20a to yield the corresponding compounds 29 and 30 (Scheme 6).

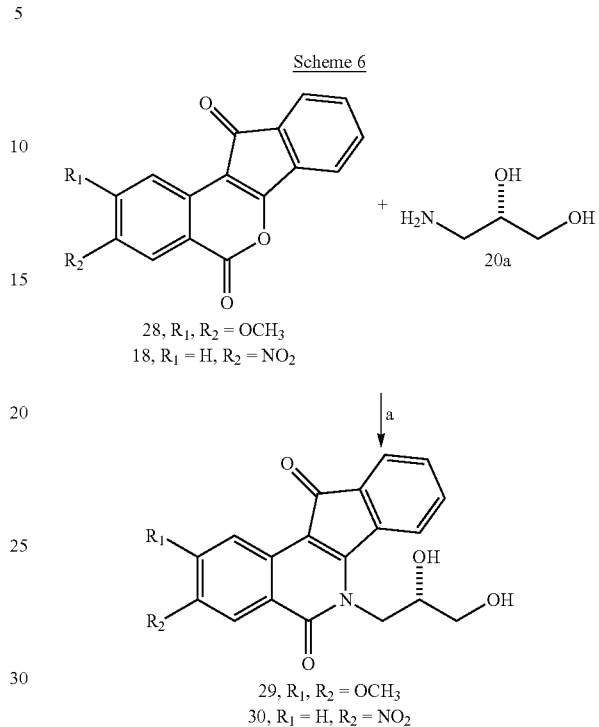

Reagents and conditions: (a) CHCl₃, reflux.

Example

Biological Results. The indenoisoquinoline analogues were tested for antiproliferative activity in the National Cancer Institute's Developmental Therapeutics Assay against cell lines derived from approximately 60 different human tumors.

After an initial one-dose screening assay (at $10^{-5}$ molar), selected compounds were tested at five concentrations ranging from $10^{-8}$ to $10^{-4}$ M. Results are reported in Table 2 as $GI_{50}$ values for selected cell lines, and overall antiproliferative potency is quantified as a mean-graph midpoint (MGM). This value can be considered an average $GI_{50}$ across all cell lines tested; compounds whose $GI_{50}$ values fall outside the concentration range tested ($10^{-8}$ to $10^{-4}$ M) are assigned $GI_{50}$ values of either $10^{-8}$ M or $10^{-4}$ M, respectively. Additionally, the values for growth percent, a measure of inhibitory activity in the initial $10^{-5}$ molar assay, are given for most compounds, including those not selected for the five-concentration screen. For comparison, Top1 and antiproliferative activity data for camptothecin (1), lead indenoisoquinolines 4 and 5, and clinical candidates 6 and 7 are included.

Top1 inhibition was measured by a compound's ability to induce enzyme-linked DNA breakage and is graded by the following semiquantitative scale relative to 1 μM camptothecin: 0, no measurable inhibitory activity; +, between 20 and 50% activity; ++, between 50 and 75% activity; +++, between 75% and 95% activity; ++++, equipotent. The 0/+score is defined as between 0 and +. It is believed that many compounds in this series may be able to act as Top1 poisons, and a representative example of Top1-linked DNA cleavage by these indenoisoquinolines may be observed in FIG. 1. As may be observed, the cleavage patterns appear to resemble indenoisoquinoline 4, with compound 30 displaying the highest potency.

indenoisoquinoline-Top1-DNA ternary complexes in which the polycyclic system of the inhibitor is similar to that of 12a.

TABLE 2

Antiproliferative Potencies and Topoisomerase I Inhibitory Activities of Substituted Indenoisoquinolines and Relevant Compounds.

| Compd | Cytotoxicity ($GI_{50}$ in μM)[a] | | | | | | | | $MGM^b$ | Growth Percent[c] | Top1 Cleavage[d] |
|---|---|---|---|---|---|---|---|---|---|---|---|
| | Lung HOP-62 | Colon HCT-116 | CNS SF-539 | Melanoma UACC-62 | Ovarian OVCAR-3 | Renal SN12C | Prostate DU-145 | Breast MCF7 | | | |
| 1[17] | 0.01 | 0.03 | 0.01 | 0.01 | 0.22 | 0.02 | 0.01 | 0.01 | $0.0405 \pm 0.0187^f$ | —[d] | ++++ |
| 4[17,40] | 1.3 | 35 | 41 | 4.2 | 73 | 68 | 37 | 1.58 | $20.0 \pm 14$ | — | ++ |
| 5[17,40] | 0.02 | 0.10 | 0.04 | 0.03 | 0.5 | <0.01 | <0.01 | <0.01 | 0.11 | — | ++++ |
| 6[19,41] | 1.78 | 1.15 | 0.04 | 0.03 | 74.1 | 0.813 | 0.155 | 0.37 | $4.64 \pm 1.25$ | — | ++++ |
| 7[19,41] | <0.01 | <0.01 | 0.037 | <0.01 | 0.085 | <0.01 | <0.01 | 0.01 | $0.079 \pm 0.023$ | — | ++++ |
| 12a | 5.01 | — | 7.41 | 5.37 | 14.5 | 6.92 | 5.75 | 4.90 | 8.71 | — | +++ |
| 12b | 3.79 | 4.47 | 5.72 | 4.36 | 16.1 | 3.77 | 2.34 | 3.04 | $6.24 \pm 0.22$ | — | 0/+ |
| 12c | 7.76 | 4.36 | 5.89 | 7.58 | 18.6 | 2.95 | 2.88 | 3.55 | 5.13 | — | ++ |
| 17a | 8.71 | 5.62 | 7.59 | 7.41 | >100 | 20.0 | 16.6 | 4.57 | 19.9 | 58.44 | ++ |
| 17b | 2.95 | 3.39 | 2.14 | 3.23 | 13.5 | 2.40 | 1.32 | 1.38 | 3.31 | 17.28 | 0 |
| 17c | — | — | — | — | — | — | — | — | — | $97.16^e$ | ++ |
| 17d | 3.23 | 3.39 | 7.94 | 2.88 | 24.0 | 2.24 | 2.75 | 1.74 | 4.07 | 34.91 | ++ |
| 17e | 6.46 | 3.39 | 11.2 | 6.31 | 13.2 | 5.01 | 3.98 | 1.90 | 7.76 | 50.62 | +++ |
| 17f | — | — | — | — | — | — | — | — | — | 69.35 | + |
| 17g | — | — | — | — | — | — | — | — | — | 67.99 | + |
| 17h | 3.23 | 4.17 | 5.75 | 2.95 | 13.8 | 3.39 | 3.31 | 1.78 | 5.75 | 49.31 | — |
| 19 | 7.35 | 5.08 | 2.61 | 2.98 | 4.26 | 17.7 | 4.76 | 0.88 | $4.60 \pm 0.53$ | 58.05 | ++++ |
| 22a | — | — | — | — | — | — | — | — | — | — | ++ |
| 22b | — | — | — | — | — | — | — | — | — | 78.60 | + |
| 22c | 17.6 | 15.9 | 14.4 | 11.7 | 25.7 | 37.1 | 23.7 | 34.4 | $15.6 \pm 2.15$ | — | + |
| 25 | 40.7 | 30.9 | 20.0 | 58.9 | 5.23 | 81.3 | 17.8 | 32.3 | 20.9 | 72.36 | + |
| 27a | 3.39 | 5.52 | 6.31 | 10.2 | 21.4 | 9.33 | 8.32 | 3.23 | 10.2 | 55.23 | +++ |
| 27b | — | — | — | — | — | — | — | — | — | 54.88 | +++ |
| 27c | 3.46 | 5.75 | 6.76 | 6.16 | 16.2 | 3.98 | 4.36 | 3.80 | 7.9 | 50.24 | + |
| 27d | 0.276 | 0.263 | 0.344 | 0.318 | 1.32 | 0.206 | 0.130 | 0.198 | $0.348 \pm 0.109$ | −23.49 | ++ |
| 29 | 0.336 | 0.230 | 0.214 | 0.144 | 0.287 | 0.501 | 0.419 | 0.097 | $0.401 \pm 0.055$ | — | +++ |
| 30 | 0.089 | 0.025 | 0.157 | 0.098 | 0.309 | 0.241 | 0.040 | 0.016 | $0.156 \pm 0.061$ | — | ++++ |

[a]The cytotoxicity $GI_{50}$ values are the concentrations corresponding to 50% growth inhibition.
[b]Mean graph midpoint for growth inhibition of all human cancer cell lines successfully tested, ranging from $10^{-8}$ to $10^{-4}$ molar.
[c]Percentage of cell growth in a one-dose assay at 10 μM. This data has recently been incorporated into the NCI protocol (implemented ca. 2006), thus, growth percent is only available for select compounds.
[d]Compound-induced DNA cleavage due to Top1 inhibition is graded by the following rubric relative to 1 μM camptothecin:
0, no measurable inhibitory activity;
+, between 20 and 50% activity;
++, between 50 and 75% activity;
+++, between 75% and 95% activity;
++++, equipotent.
The 0/+ ranking is between 0 and +.
[e]Some compounds were not selected for further testing, refer to text for details.
[f]For MGM $GI_{50}$ values in which a standard error appears, the $GI_{50}$ values for individual cell lines are the average of two determinations; values without standard error are from one determination. The values for 1, 4, 5, 6, and 7 are from many determinations.

Without being bound by theory, the data for the short-chain alcohol and diol substituents may, in part, be used to explain the results of aldopentose and hexose substitution. The Top1 inhibitory activity of compounds 12a and 12b appears to differ (+++ and 0/+, respectively). An attempt to explain this difference was made through analysis of hypothetical binding modes using molecular modeling and docking. Both compounds were docked with GOLD using a defined active site centroid in a mutant, solvated Top1-DNA complex.] The ternary complexes containing the highest-ranked ligand poses were then minimized and visualized with SYBYL 8.1. Although the docking protocol was extensively validated, the top ligand poses appeared to be dependent upon the assigned charge sets. Nonetheless, several docking runs indicated that a mixture of two dominant poses for compound 12a were returned regardless of the charge set used, and these poses had similar GOLD fitness scores (between 72-75). A "normal" mode was returned as the top pose when MMFF94s charges were assigned to the ligand. In this mode, the position of the aromatic core is believed to be close to that in crystallized indenoisoquinoline-Top1-DNA ternary complexes in which the polycyclic system of the inhibitor is similar to that of 12a. The ketone hydrogen bonds with Arg364 and the polar side chain appears to project into the major groove.

When Gasteiger-Hückel charges were assigned instead, a "flipped" binding mode was returned as the top-ranked pose (although normal modes were also returned as alternates). Interestingly, flipped binding modes were not returned in the top five poses during the docking validation runs with camptothecin (1), topotecan (2), and indenoisoquinoline 11, regardless of the ligand, charges, or force field used. In this binding mode, the ligand is flipped 180° along the long axis of the indenoisoquinoline and 180° relative to the short axis, which appears to be positioning the lactam carbonyl in a location to hydrogen bond with Arg364. The side chain is thus calculated to project into an open area of the minor groove. It is believed that there is currently no literature evidence available to support this binding mode for indenoisoquinolines (ab initio calculations indicate normal modes are more favorable), however, X-ray crystallography appears to indicate that norindenoisoquinolines, which are believed to share a similar aromatic core, bind in a flipped mode, and ab initio calculations indicate that the flipped mode of norindenoisoquinolines is more favorable. Moreover, the GOLD fitness scores for 12a binding in the "normal" mode (72.98) and the "flipped mode" (74.30) were similar, which may be taken as indicating a small difference in binding energies between the two modes. On the other hand, the prior ab initio calculations carried out at the MP2 level, which appear to indicate a preference for binding in the "normal mode", are likely to be more accurate because they take dispersion into consideration. They also appear to agree with X-ray crystallography studies that show compound 11 binding in the "normal mode".

Without being bound by theory, overall, the molecular modeling results may indicate that both binding modes are theoretically possible and should be considered. In both cases, the aromatic core of the indenoisoquinoline appears to be well intercalated into the complex without any visible steric hindrance, projecting the diol side chain beyond the flanking base pairs where it is free to interact with the surrounding structures. In both binding modes, polar contacts and water-mediated H-bonds are observed. For compound 12a, without being bound by theory, the ketone of the aromatic core is predicted to hydrogen-bond with Arg364. Additional contacts (including water-mediated H-bonds) are formed with Met428, Asn352, and two flanking base pairs. Similar networks of water have been reported to stabilize the side chains in similar models of polar indenoisoquinolines and aromathecins. In the flipped binding mode, most major-groove contacts appear to be absent, but the diol side chain appears to form two H-bonds in the minor groove: with the flanking base pair Tgp11, and the amino acid Asp533. The lactam carbonyl also appears to bind to Arg364. For compound 12b, only the normal binding mode was returned by GOLD regardless of assigned charge set.

Without being bound by theory, it is believed that the possibility of alternate binding modes makes it difficult to determine the effect of stereochemistry on the potency of Top1 inhibition. Similar interactions within the ternary complex are observed, and there are no apparent differences between the normal binding modes of the polycyclic systems of compounds 12a and 12b. Compound 12b, in normal mode, also appears to form H-bonds (including water-mediated) with two flanking base pairs, Arg364, and Tyr426.

It has been observed that the cytotoxic effects exerted by these two compounds, and others in this series, appear to be similar despite having differing Top1 inhibitory activities.

In all the models and binding modes, the 2'-hydroxyl of the diols appears to form a hydrogen bond. It has been found herein that indenoisoquinolines 22a-c appear to exhibit a loss of Top1 inhibition relative to compounds 12a and 27a-b, regardless of stereochemistry. Without being bound by theory, the lower activity of 22a-c may be due to the loss of hydrogen bonding between the 2'-hydroxyl and surrounding structures. Additionally, the ketone analogue 25 appears to have a lower Top1 inhibition potency, which, without being bound by theory, may indicate that the role of the secondary hydroxyl of 12a may be to serve as a hydrogen-bond donor.

Example

Indenoisoquinolines 27a and 27b, which lack a primary hydroxyl group, demonstrate no reduction in Top1 inhibition when compared to the reduction observed for indenoisoquinolines lacking the secondary hydroxyl. Without being bound by theory, it is believed that these results may indicate that the primary alcohol may not be as important as the 2'-hydroxyl substituent, despite the contacts it forms in the models. Unlike compounds 12a-12c, however, the stereochemistry of the secondary alcohol appears to have little effect on Top1 inhibition (cf. compounds 27a and 27b, it is unknown why the racemate 27c has lower activity). Without being bound by theory, this result, along with the observed absence of a stereochemical effect for 22a and 22b, may indicate that the presence of both the primary and secondary alcohol leads to the differences in activity observed initially in 12a and 12b.

It is believed that compound 27d exists in the racemic form and its Top1 inhibitory activity appears to be comparable to the activity of racemate 12c, which, without being bound by theory, may be taken as indicating that the primary amine does not improve affinity in the ternary complex. It has been reported that the hydroxyl-to-amine change did not appear to be effective at enhancing Top1 inhibition for indolocarbazoles. A difference between these two racemates is observed in their cytotoxicities, however. Indenoisoquinoline 12c has an MGM $GI_{50}$ of 5.13 µM, whereas indenoisoquinoline 27d appears to be more potent with an MGM $GI_{50}$ of 0.348 µM. The source of this effect, but, without being bound by theory, one possibility is that the protonated primary amine aids in targeting the drug to negatively charged DNA or enters cells via an amino acid or polyamine transport system.

Example

The dimethoxy- and nitro-analogues of compound 12a appeared to be more cytotoxic than the parent compound (29, 0.401 µM; 30, 0.156 µM) while maintaining Top1 inhibition. Without being bound by theory, it is believed that the increase in anti-Top1 potency of 30 is associated with hydrogen bonding between the nitro substituent and enzyme residues. Additionally, it is possible that the strong electron-withdrawing nature of the nitro substituent may increase the π-stacking interaction between the indenoisoquinoline aromatic core and flanking DNA bases by enabling charge-transfer complex formation and increasing charge complementarity between the intercalator and the neighboring bases. EXAMPLE. Indenoisoquinolines 17a-h, derived from aldopentose and aldohexose sugars, were also assayed. Although these indenoisoquinolines appeared to demonstrate a fairly small range of MGM $GI_{50}$ values (3 µM to 20 µM), Top1 inhibitory activity appeared to vary significantly. The compounds derived from D-arabinose (17a), D-glucose (17c), D-xylose (17d) and D-lyxose (17e) appear to demonstrate the most potent Top1 inhibitory activity (++/+++), which may indicate that carbohydrate substituents can be successfully combined with the indenoisoquinoline system. It has been reported that arabityl substitution produced indolocarbazoles with significant DNA-targeting activity as well. The remaining compounds [those derived from ribose (17b), mannose (17f), and galactose (17g)] appear to possess only weak Top1 inhibitory activity (0 or +), which, without being bound by theory, may be demonstrating a strong stereochemical dependence.

It is believed that it may be a difficult task to disentangle the full effects that sugar-substitution may have on bioactivity. Unlike in previous reported studies performed with indolocarbazoles, the presence of additional hydrogen bond donors does not appear to linearly increase activity (compare compounds 17e and 17f), which, without being bound by theory, may be taken as indicating that the orientation of the hydrogen-bond donors may be a major determinant.

Due to the limitation of predictive reliability of the molecular models and the possibility of multiple binding modes, an analogous study with hypothetical models of carbohydrate-derived indenoisoquinolines was not performed. Without being bound by theory, it is possible that these structures may make more polar contacts than compounds 12a and 12b, and it is believed that increasing the degree of ligand flexibility (as in these carbohydrate side chains) may further erode the reliability of docking studies. Without being bound by theory, it is possible that the differences in Top1 inhibitory activity may be due to a complex relationship between orientation (e.g. possible interaction between adjacent hydroxyls directed by stereochemistry, as proposed for 12a and 12b), intramolecular hydrogen bonding, and side-chain flexibility. Without being bound by theory, it is suggested that perhaps the relative stereochemistry of the hydroxyl groups may serve to create an "active" or more sterically favored conformation in some cases.

Although it is difficult to definitively explain the stereochemical determinants of the SAR, it may be worth noting that similar trends have been reported for other Top1 inhibitors. It has been reported that the stereochemistry of the glycosidic bond (i.e., α vs β) between the carbohydrate and the indole moieties of indolocarbazoles has an effect on biological activity, and the stereochemistry of the sugar itself may be responsible for DNA-sequence recognition and binding. Differences in Top1 inhibition activity (but interestingly, not cytotoxicity) between indolocarbazoles substituted with different cyclic sugars and disaccharides have also been observed and it has been proposed that there are no "universal" Top1 SAR trends for carbohydrate substituents. Stereochemical effects have also been observed in topoisomerase-poisoning saccharide analogues of anthracyclines. Even camptothecin (1) reportedly is believed to exhibit a dramatic relationship between stereochemistry and biological activity: natural camptothecin exists with the 20-(S)-configuration, and inversion of the stereochemistry at this position attenuates the Top1 inhibitory activity greatly.

Example

General. Solvents and reagents were purchased from commercial vendors and were used without any further purification. Melting points were determined using capillary tubes with a Mel-Temp apparatus and are uncorrected. Infrared spectra were obtained using KBr pellets or on salt plates using $CHCl_3$ as the solvent. IR spectra were recorded using a Perkin-Elmer 1600 series or Spectrum One FTIR spectrometer. $^1H$ NMR spectra were recorded at 300 MHz using a Bruker ARX300 spectrometer with a QNP probe. Mass spectral analyses were performed at the Purdue University Campus-Wide Mass Spectrometry Center. ESIMS was performed using a FinniganMAT LCQ Classic mass spectrometer system. EI/CIMS was performed using a Hewlett-Packard Engine or GCQ FinniganMAT mass spectrometer system. Combustion microanalyses were performed at the Purdue University Microanalysis Laboratory using a Perkin-Elmer Series II CHNS/O model 2400 analyzer. All reported values are within 0.4% of the calculated values; purity of biologically important compounds is ≥95%. Analytical thin-layer chromatography was carried out on Baker-flex silica gel IB2-F plates and compounds were visualized with short wavelength UV light and $KMnO_4$ staining. Silica gel flash chromatography was performed using 230-400 mesh silica gel and ion-exchange chromatography was performed using Dowex 50W-X8-100 resin activated with $H_2O$. Lactones 16, 18, and 28 were prepared according to literature procedures.

Example

General Procedure for Preparation of Sugar Oximes (14a-h). Hydroxylamine hydrochloride (0.976-10.8 g, 14.0-155 mmol) was diluted with absolute EtOH (6-65 mL) or an equivalent amount of dry MeOH. Two drops of phenolphthalein (1% solution in EtOH) were added. A solution of sodium methoxide (10.0-133 mmol) or an equivalent amount of sodium ethoxide (in the case of 13g) in EtOH or MeOH (6-90 mL) was added slowly to the suspension, upon which a white precipitate formed. Addition of base was halted when the mixture stayed pink for approximately one minute (or the pH was titrated back to this point by addition of minimal hydroxylamine hydrochloride). The mixture was stirred for several minutes and filtered to remove salts. The filtrate was warmed to 70° C., and an aldopentose or aldohexose (sugars 13a-h, 1.0-12.0 g, 5.56-66.0 mmol) was added in small portions. The mixture was stirred at 70° C. until the sugar had completely dissolved (10 min-4 h; typical time, 20 min) and cooled to room temperature. The oximes either precipitated from solution (compounds 14a, 14b, and 14f-h) or were isolated as semi-solids or syrups after concentration and drying in vacuo (compounds 14c-e).

Example

D-Arabinose Oxime (14a). By the general procedure, hydroxylamine hydrochloride (5.90 g, 84.9 mmol), NaOMe (4.54 g, 84.0 mmol) and D-arabinose (13a, 5.45 g, 36.3 mmol) afforded the title compound [a mixture of 70% (E)-oxime and 30% (Z)-oxime] as a white microcrystalline solid (4.54 g, 76%): mp 128-136° C. (lit mp 135-136° C.). $^1H$ NMR ($D_2O$) δ 7.55 (dd, J=6.1, 1.8 Hz, 1H), 4.47 (dd, J=5.9, 2.7 Hz, 1H), 3.80-3.60 (m, 5H). Some of the hydroxyl groups are not visible due to exchange with residual water. Small resonances at 6.91 (dd, J=5.6, 1.8 Hz, 1H) and 5.07 (dd, J=5.6, 2.0 Hz, 1H) ppm [corresponding to the (Z)-oxime] are visible.

Example

D-Ribose Oxime (14b). By the general procedure, hydroxylamine hydrochloride (5.90 g, 84.9 mmol), NaOMe (~4.75 g, 88.0 mmol) and D-ribose (13b, 5.45 g, 36.3 mmol) afforded the title compound [>90% (Z)-oxime] as a white microcrystalline solid (4.13 g, 69%) after filtration; additional product crystallized from the mother liquor upon standing: mp 137-140° C. (literature value mp 138-139° C.). $^1H$ NMR ($D_2O$) δ 6.86 (d, J=6.3 Hz, 1H), 5.05 (dd, J=6.2, 3.7 Hz, 1H), 3.80-3.54 (m, 5H). Some of the hydroxyl groups are not visible due to exchange with residual water. Very small resonances at 7.50 (d, J=6.9 Hz, 1H) and 4.40 (m, 1H) ppm [corresponding to the (E)-oxime] are visible.

Example

D-Glucose Oxime (14c). By the general procedure, hydroxylamine hydrochloride (10.8 g, 155 mmol), NaOMe (7.2 g, 133 mmol) and D-glucose (13c, 12.0 g, 66.6 mmol) afforded the crude product (13.0 g, 100% with some residual solvent) as a colorless semisolid. Resonances corresponding to the carbonyl protons of (E)- and (Z)-oximes were visible (along with some unreacted aldehyde) and the crude product was used as such without further purification.

Example

D-Xylose Oxime (14d). By the general procedure, hydroxylamine (2.82 g, 40.6 mmol), NaOMe (2.19 g, 40.6 mmol) and D-xylose (13d, 2.50 g, 16.6 mmol) afforded the title compound [80% (E)-oxime] as a colorless, clear syrup (2.93 g, 100% with residual solvent) after drying in vacuo. $^1H$ NMR (D$_2$O) δ 7.50 (d, J=6.8 Hz, 1H), 4.35 (d, J=5.7 Hz, 1H), 3.75-3.56 (m, 5H). Some of the hydroxyl groups are not visible due to exchange with residual water. Resonances at 6.86 (d, J=5.6 Hz, 1H) and 4.95 (m, 1H) ppm [corresponding to the (Z)-oxime] are visible; ESIMS m/z (rel. intensity) 188 (MNa$^+$, 100).

Example

D-Lyxose Oxime (14e). By the general procedure, hydroxylamine hydrochloride (1.58 g, 22.8 mmol), NaOMe (1.23 g, 22.8 mmol) and D-lyxose (13e, 1.40 g, 9.32 mmol) afforded the title compound [85% (E)-oxime] as a pale-yellow semisolid (1.61 g, 100% with residual solvent) after drying in vacuo. $^1$H NMR (D$_2$O) δ 7.51 (d, J=7.0 Hz, 1H), 4.25 (t, J=7.4 Hz, 1H), 3.84-3.76 (m, 1H), 3.70-3.55 (m, 3H). Some of the hydroxyl groups are not visible due to exchange with residual water. Resonances at 6.90 (d, J=6.8 Hz, 1H) and 4.93 (m, 1H) ppm [corresponding to the (Z)-oxime] are visible.

Example

D-Mannose Oxime (14f). By the general procedure, hydroxylamine hydrochloride (2.24 g, 32.2 mmol), NaOMe (1.50 g, 27.8 mmol), and D-mannose (13f, 2.50 g, 14.0 mmol) afforded the title compound [>90% (E)-oxime] as a white solid (2.23 g, 82%): mp 173-176° C. [lit mp 183-185° C. (dec)]. $^1$H NMR (CD$_3$OD) δ 7.44 (d, J=6.9 Hz, 1H), 4.23 (dd, J=8.2, 6.9 Hz, 1H), 3.86-3.77 (m, 3H), 3.73-3.61 (m, 2H). Some of the hydroxyl groups are not visible due to exchange with residual water. A small resonance at ~6.80 ppm [corresponding to the (Z)-oxime] is visible; CIMS m/z (rel. intensity) 196 (MH$^+$, 84), 178 [(MH$^+$+H$_2$O), 14], 103 [(MH$^+$—3H$_2$O—C$_3$H$_3$), 100].

Example

D-Galactose Oxime (14g). By the general procedure, hydroxylamine hydrochloride (0.95 g, 13.7 mmol), NaOEt (0.64 g, 9.45 mmol), and D-galactose (13g, 1.0 g, 5.56 mmol) afforded the title compound [a mixture of 50% (E)- and 50% (Z)-oxime] as a white solid (1.01 g, 94%): mp 172-174° C. (lit mp 176° C.). $^1$H NMR (CD$_3$OD) (E)-oxime: δ 7.50 (d, J=6.6, 1H), 5.17 (dd, J=5.5, 1.7 Hz, 1H), 3.88-3.83 (m, 1H), 3.72-3.60 (m, 5H); (Z)-oxime: 6.80 (d, J=5.5 Hz, 1H), 4.48 (dd, J=6.6, 1.5 Hz, 1H), 3.88-3.83 (m, 1H), 3.72-3.60 (m, 5H). Some of the hydroxyl groups are not visible due to exchange with residual water; ESIMS m/z (rel. intensity) 218 (MNa$^+$, 51), 195 (MH$^+$, 100).

Example

D-Allose Oxime (14h). By the general procedure, hydroxylamine hydrochloride (0.973 g, 14.0 mmol), NaOMe (0.541 g, 10.0 mmol) and D-allose (13h, 0.900 g, 5.00 mmol) afforded the title compound [>95% (Z)-oxime] as a white solid (0.668 g, 68%): mp 140-142° C. $^1$H NMR (CD$_3$OD) δ 6.77 (d, J=6.2 Hz, 1H), 5.08 (dd, J=6.2, 3.6 Hz, 1H), 3.88 (dd, J=7.6, 3.6 Hz, 1H), 3.82-3.71 (m, 2H), 3.66-3.60 (m, 2H). The hydroxyl groups are not visible due to exchange with residual water. Very small resonances at ~7.40 and ~4.40 ppm [corresponding to the (E)-oxime are visible; ESIMS m/z (rel. intensity) 412 (2MNa$^+$, 100), 218 (MNa$^+$, 65), 195 (MH$^+$, 4).

Example

General Procedure for Oxime Reduction (to yield amines 15a-h). The sugar oxime (0.6-10 g, 3.06-51.2 mmol) was diluted with glacial AcOH (10-65 mL), and Pt(IV)O$_2$ (0.06-0.600 g, generally around 1% w/w was sufficient) was added. The mixture was hydrogenated with shaking on a Parr apparatus at 35-45 psi, for between 18 h and 3.5 days, or until the mixture was clear. The mixture was then filtered to remove the catalyst, concentrated, dissolved in H$_2$O (80-250 mL) and loaded onto an ion-exchange column packed in H$_2$O. The column was washed with H$_2$O (80-200 mL) after loading, and then the desired aminodeoxyalditol was eluted using NH$_4$OH (3 N, between 80-250 mL). The alkaline fraction was concentrated to yield the crude aminodeoxyalditols (15a-h), which were used without further purification to synthesize indenoisoquinolines.

Example

D-Arabitylamine (15a). From 14a (3.00 g, 18.2 mmol), the general procedure afforded the desired product as a dark yellow syrup (2.77 g, 100% with some residual water). $^1$H NMR (CD$_3$OD) δ 3.80-3.50 (m, 6H), 3.90-2.72 (m, 2H). Some of the hydroxyl groups and the primary amine are not visible due to exchange with residual water.

Example

D-Ribitylamine (15b). From 14b (3.00 g, 18.2 mmol), the general procedure afforded the desired product as a light brown syrup (2.78 g, 100% with some residual water). $^1$H NMR (CD$_3$OD) δ 3.77-3.52 (m, 5H), 2.90-2.73 (m, 2H). Hydroxyl groups and the primary amine are not visible due to exchange with residual water.

Example

D-Glucamine (15c). From crude 14c (10.0 g, 51.2 mmol), the general procedure afforded the desired product as a dark brown oil (6.37 g, 70%). $^1$H NMR resonances were consistent with crude D-glucamine and this material was used without further purification to prepare 17c and 19.

Example

D-Xylitylamine (15d). From 14d (2.93 g, 17.7 mmol), the general procedure afforded the desired product as a dark yellow syrup (2.16 g, 81%). $^1$H NMR (D$_2$O) δ 3.75-3.50 (m, 5H), 2.76-2.61 (m, 2H). Hydroxyl groups and the primary amine are not visible due to exchange with the solvent; ESIMS m/z (rel. intensity) 152 (MH$^+$, 100).

Example

D-Lyxitylamine (15e). From 14e (1.61 g, 9.70 mmol), the general procedure afforded the desired product as a brown syrup (1.27 g, 87%). $^1$H NMR (CD$_3$OD) δ 3.87 (t, J=5.7 Hz, 1H), 3.65-3.59 (m, 3H), 3.44 (d, J=7.0 Hz, 1H), 2.97 (dd, J=13.2, 3.5 Hz, 1H), 2.91 (dd, J=13.1, 7.1 Hz, 1H). Hydroxyl groups and the primary amine are not visible due to exchange with residual water; ESIMS m/z (rel. intensity) 286 [(2MH$^+$—NH$_3$)$^+$, 100], 152 (MH$^+$, 18).

Example

D-Mannitylamine (15f). From 14f (2.00 g, 12.0 mmol), the general procedure afforded the desired product as a dark-brown oil (1.35 g, 97%). $^1$H NMR (CD$_3$OD) δ 3.86-3.59 (m, 6H), 3.29-3.22 (m 1H), 2.99 (dd, J=12.2, 8.0 Hz, 1H).

Hydroxyl groups and the primary amine are not visible due to exchange with residual water; ESIMS m/z (rel. intensity) 182 (MH$^+$, 86).

Example

D-Galactitylamine (15g). From 14g (1.01 g, 5.17 mmol), the general procedure afforded the desired product as a dark-brown oil (0.95 g, 100% with some residual water). $^1$H NMR (CD$_3$OD) δ 4.11-4.00 (m, 1H), 3.80 (dt, J=1.3, 6.4 Hz, 1H) 3.64-3.51 (m, 5H), 3.10-2.97 (m, 2H). Some hydroxyl groups and the primary amine are not visible due to exchange with residual water; CIMS m/z (rel. intensity) 182 (MH$^+$, 100).

Example

D-Allitylamine (15h). From 14h (0.600 g, 3.01 mmol), the general procedure afforded the desired product as a dark-brown oil (0.475 g, 86%). $^1$H NMR (CD$_3$OD) δ 4.10-3.98 (m, 1H), 3.86-3.53 (m, 5H), 3.30-2.90 (m, 2H). Hydroxyl groups and the primary amine are not visible due to exchange with residual water; ESIMS m/z (rel. intensity) 346 [(2MH$^+$—NH$_3$)$^+$, 100], 182 (MH$^+$, 2).

Example

General Procedure for Preparation of Indenoisoquinolines 12a-c, 17a-h, 19, 22a-c, 25, 27a-d, 29, and 30. A solution of the appropriate lactone, 16 (0.040-0.254 g, 0.14-1.02 mmol), 18 (0.040-0.215 g, 0.136-0.733 mmol), or 28 (0.100 g, 0.324 mmol) and the primary amine (0.05-0.36 g, 0.33-2.20 mmol, 2.0-3.0 equiv.) in either MeOH (15-125 mL) or CHCl$_3$ (20-70 mL) was heated to reflux. After 2-36 h (typical time: 18 h), the reaction mixture was cooled to room temperature. In cases where precipitation resulted, the precipitate was collected by filtration and washed with CHCl$_3$ (50-300 mL). In cases where the product was soluble in the reaction solvent, the reaction mixture was concentrated and the residue was dissolved in CHCl$_3$ (20-70 mL). The solution was washed with H$_2$O (3×10-30 mL), sat. NaCl (in some cases), dried over anhydrous sodium sulfate, and concentrated to afford the desired compounds after chromatography (as described for individual compounds).

Example (n)-5,6-Dihydro-6-[(2',3'-dihydroxypropyl)]-5,11-dioxo-11H-indeno[1,2-c]isoquinoline (12a). From lactone 16 (0.150 g, 0.604 mmol) and alcohol 20a (0.110 g, 1.21 mmol) in MeOH (50 mL), the general procedure afforded the title compound as a yellow-orange solid (0.159 g, 82%) after purification by flash column chromatography (SiO$_2$, eluting with a gradient of CHCl$_3$ to 5% MeOH in CHCl$_3$): mp 200-205° C. IR (KBr) 3400, 1705, 1655, 1611, 1503 cm$^{-1}$; $^1$H NMR (DMSO-d$_6$) δ 8.61 (d, J=8.1 Hz, 1H), 8.23 (d, J=8.1 Hz, 1H), 8.07 (d, J=7.4 Hz, 1H), 7.85 (m, 1H), 7.56-7.46 (m, 4H), 5.14 (d, J=5.1 Hz, 1H), 4.99 (t, J=5.6 Hz, 1H), 4.60-4.50 (m, 2H), 4.00-3.90 (m, 1H), 3.60 (t, J=5.5 Hz, 2H); ESIMS m/z (rel. intensity) 322 (MH$^+$, 73), 304 [(MH$^+$+H$_2$O)$^+$, 100]. Anal. Calcd for C$_{19}$H$_{15}$NO$_4$: C, 71.02; H, 4.71; N, 4.36. Found: C, 70.73; H, 4.60; N, 4.31.

Example (2'R)-5,6-Dihydro-6-[(2',3'-dihydroxypropyl)]-5,11-dioxo-11H-indeno[1,2-c]isoquinoline (12b). From lactone 16 (0.100 g, 0.403 mmol) and alcohol 20b (0.073 g, 0.806 mmol) in MeOH (50 mL), the general procedure afforded the title compound as a yellow-orange solid (0.096 g, 74%) after washing with EtOAc-hexanes: mp 200-205° C. IR (KBr) 3349, 1704, 1641, 1611, 1503, 1425, 1316, 1045, 879, 757 cm$^{-1}$; $^1$H NMR (DMSO-d$_6$) δ 8.61 (d, J=7.8 Hz, 1H), 8.22 (d, J=8.1 Hz, 1H), 8.07 (d, J=7.6 Hz, 1H), 7.84 (m, 1H), 7.56-7.43 (m, 4H), 5.14 (d, J=5.1 Hz, 1H), 4.99 (t, J=5.1 Hz, 1H), 4.60-4.47 (m, 2H), 4.00-3.90 (m, 1H), 3.60 (t, J=5.3 Hz, 2H); ESIMS m/z (rel. intensity) 321 (MH$^+$, 73), 304 [(MH$^+$+H$_2$O)$^+$, 100]. Anal. Calcd for C$_{19}$H$_{15}$NO$_4$: C, 71.02; H, 4.71; N, 4.36. Found: C, 70.86; H, 4.66; N, 4.34.

Example (2'RS)-5,6-Dihydro-6-[(2',3'-dihydroxypropyl)]-5,11-dioxo-11H-indeno[1,2-c]isoquinoline (12c). From lactone 16 (0.140 g, 0.604 mmol) and alcohol 20c (0.110 g, 1.21 mmol) in MeOH (50 mL), the general procedure afforded the title compound as a yellow-orange solid (0.150 g, 77%) after purification by flash column chromatography (SiO$_2$, eluting with a gradient of CHCl$_3$ to 5% MeOH in CHCl$_3$): mp 209-212° C. IR (KBr) 3400, 1705, 1655, 1611, 1503 cm$^{-1}$; $^1$H NMR (DMSO-d$_6$) δ 8.61 (d, J=8.1 Hz, 1H), 8.23 (m, 1H), 8.07 (d, J=7.4 Hz, 1H), 7.85 (m, 1H), 7.56-7.46 (m, 4H), 5.14 (d, J=5.1 Hz, 1H), 4.99 (d, J=5.6 Hz, 1H), 4.57 (m, 2H), 4.00 (m, 1H), 3.60 (t, J=5.5 Hz, 2H); ESIMS m/z (rel. intensity) 322 (MH$^+$, 48), 304 [(MH$^+$+H$_2$O)$^+$, 100]. Anal. Calcd for C$_{19}$H$_{15}$NO$_4$.0.2H$_2$O: C, 70.23; H, 4.78; N, 4.31. Found: C, 69.85; H, 4.38; N, 4.66.

Example (2'R,3'S,4'R)-5,6-Dihydro-6-(2',3',4',5'-tetrahydroxypentyl)-5,11-dioxo-11H-indeno[1,2-c]isoquinoline (17a). From lactone 16 (0.061 g, 0.241 mmol) and amine 15a (0.050 g, 0.331 mmol) in MeOH (20 mL), the general procedure afforded the title compound as a red solid (0.067 g, 72%) that was used without further purification: mp 231-233° C. IR (KBr) 3281, 2925, 1705, 1658, 1501, 1457, 1378 cm$^{-1}$; $^1$H NMR (DMSO-d$_6$) δ 8.61 (d, J=8.1 Hz, 1H), 8.20 (t, J=7.4 Hz, 1H), 7.81 (t, J=7.4 Hz, 1H), 7.54-7.44 (m, 4H), 4.92 (d, J=7.5 Hz, 1H), 4.84 (d, J=5.9 Hz, 1H), 4.62-4.41 (m, 4H), 4.32 (m, 1H), 3.66 (t, J=5.8 Hz, 1H), 3.54-3.34 (m, 4H); ESIMS m/z (rel. intensity) 381 [(M–H$^+$)$^-$, 100]. Anal. Calcd for C$_{21}$H$_{19}$NO$_6$.0.5H$_2$O: C, 64.61; H, 5.16; N, 3.39. Found: C, 64.27; H, 5.10; N, 3.39.

Example (2'S,3'S,4'R)-5,6-Dihydro-6-(2',3',4',5'-tetrahydroxypentyl)-5,11-dioxo-11H-indeno[1,2-c]isoquinoline (17b). From lactone 16 (0.254 g, 1.02 mmol) and amine 15b (0.316 g, 2.05) in MeOH (125 mL), the general procedure afforded the title compound as an orange solid (0.295 g, 75%) after flash column chromatography (SiO$_2$, eluting with a gradient of CHCl$_3$ to 20% MeOH in CHCl$_3$): mp 218-221° C. IR (KBr) 3476, 3380, 1691, 1656, 1504, 1069, and 761 cm$^{-1}$; $^1$H NMR (DMSO-d$_6$) δ 8.60 (d, J=7.8 Hz, 1H), 8.21-8.18 (m, 2H), 7.83 (m, 1H), 7.54-7.42 (m, 4H), 5.19 (d, J=5.0 Hz, 1H), 4.98 (d, J=5.5 Hz, 1H), 4.77 (d, J=4.5 Hz, 1H), 4.68-4.62 (m, 3H), 4.49 (t, J=5.4 Hz, 1H), 4.22-4.10 (m, 1H), 3.67-3.61 (m, 3H), 3.48-3.45 (m, 1H); ESIMS m/z (rel. intensity) 382 (MH$^+$, 89), 364 [(MH$^+$+H$_2$O)$^+$, 100]. Anal. Calcd for C$_{21}$H$_{19}$NO$_6$.0.39H$_2$O: C, 64.94; H, 5.13; N, 3.61. Found: C, 64.56; H, 4.73; N, 4.00.

Example (2'S,3'R,4'R,5'R)-5,6-Dihydro-6-(2',3',4',5',6'-pentahydroxyhexyl)-5,11-dioxo-11H-indeno[1,2-c]isoquinoline (17c). From lactone 16 (0.200 g, 0.806 mmol) and amine 15c (0.363 g, 2.0 mmol) in MeOH (60 mL), the general procedure afforded the title compound as an orange solid (0.067 g, 20%) after flash column chromatography (SiO$_2$, eluting with a gradient of CHCl$_3$ to 20% MeOH in CHCl$_3$): mp 240-244° C. IR (KBr) 3430, 2085, 1627, 1549, 1504, 1424, 1316, 1269, 1179 cm$^{-1}$. $^1$H NMR (DMSO-d$_6$) δ 8.61 (d, J=8.1 Hz, 1H), 8.22 (t, J=8.3 Hz, 2H), 7.81 (t, J=7.0 Hz, 1H), 7.54-7.44 (m, 4H), 5.13 (d, J=4.9 Hz, 1H), 4.85 (d, J=6.4 Hz, 1H), 4.70-4.60 (m, 1H), 4.60-4.54 (m, 3H), 4.43 (t, J=5.4 Hz, 1H), 4.20-4.10 (br m, 1H), 3.90-3.80 (br m, 1H), 3.64-3.40 (m, 4H); negative ion ESIMS m/z (rel. intensity) 821 [2(M+H$^+$)$^-$, +H$^+$, 100], 410 [(M+H$^+$)$^-$, 92]. Anal. Calcd for C$_{22}$H$_{21}$NO$_7$.1H$_2$O: C, 61.53; H, 5.40; N, 3.26. Found: C, 61.78; H, 5.42; N, 3.47.

Example (2'S,3'R,4'R)-5,6-Dihydro-6-(2',3',4',5'-tetrahydroxypentyl)-5,11-dioxo-11H-indeno[1,2-c]isoquinoline (17d). From lactone 16 (0.100 g, 0.403 mmol) and amine 15d (0.251 g, 1.66 mmol) in MeOH (60 mL), the general procedure afforded the title compound as a red solid (0.028 g, 18%) that was used without further purification: mp 220-224° C. IR (film) 3374, 1701, 1625, 1549, 1506, 1032, 884, 757 cm$^{-1}$; $^1$H NMR (DMSO-d$_6$) δ 8.63 (d, J=7.8 Hz, 1H), 8.25-8.22 (m, 2H), 7.85 (t, J=6.9 Hz, 1H), 7.57-7.44 (m, 4H), 5.05 (d, J=5.1 Hz, 1H), 4.87 (d, J=6.2 Hz, 1H), 4.79-4.53 (m, 4H), 4.06-4.16 (br m, 1H), 3.40-3.56 (m, 5H); EIMS m/z (rel. intensity) 247 [(M-C$_5$H$_{10}$O$_4$)$^+$, 100], 381 (M$^+$, 5). Anal. Calcd for C$_{21}$H$_{19}$NO$_6$.1.0H$_2$O: C, 63.15; H, 5.30; N, 3.51. Found: C, 63.01; H, 5.03; N, 3.54.

Example (2'R,3'R,4'R)-5,6-Dihydro-6-(2',3',4',5'-tetrahydroxypentyl)-5,11-dioxo-11H-indeno[1,2-c]isoquinoline (17e). From lactone 16 (0.112 g, 0.450 mmol) and amine 15e (0.136 g, 0.900 mmol) in MeOH (30 mL), the general procedure afforded the title compound as an orange solid (0.024 g, 5%) after flash column chromatography (SiO$_2$, eluting with a gradient of CHCl$_3$ to 20% MeOH in CHCl$_3$): mp 183-185° C. IR (KBr) 3351, 2924, 1756, 1738, 1704, 1655, 1609, 1548, 1504, 1429, 1316, 1267, 1197 cm$^{-1}$; $^1$H NMR (DMSO-d$_6$) δ 8.61 (d, J=8.1 Hz, 1H), 8.22 (d, J=8.1 Hz, 1H), 8.08 (d, J=7.6 Hz, 1H), 7.83 (t, J=7.6 Hz, 1H), 7.58-7.43 (m, 4H), 5.08 (d, J=5.7 Hz, 1H), 4.82 (d, J=6.9 Hz, 1H), 4.72-4.53 (m, 3H), 4.36 (d, J=6.6 Hz, 1H), 4.10-4.09 (br m, 1H), 3.70-3.42 (m, 4H); CIMS m/z (rel. intensity) 382 (MH$^+$, 50), 364 [(MH$^+$+H$_2$O)$^+$, 100]. Anal. Calcd for C$_{21}$H$_{19}$NO$_6$.1.1H$_2$O: C, 62.95; H, 5.32; N, 3.50. Found: C, 62.56; H, 4.91; N, 3.32.

Example (2'R, 3'R, 4'R, 5'R)-5,6-Dihydro-6-(2',3',4',5',6'-pentahydroxyhexyl)-5,11-dioxo-11H-indeno[1,2-c]isoquinoline (17f). From lactone 16 (0.137 g, 0.550 mmol) and amine 15f (0.250 g, 1.38 mmol) in MeOH (45 mL), the general procedure afforded the desired product as an orange solid (0.097 g, 43%) after washing with CHCl$_3$ (~500 mL): mp 244-246° C. IR (KBr) 3450, 3302, 3235, 3071, 2969, 1713, 1654, 1634, 1610, 1549, 1504, 1414, 1317, 1200, 1075, 1012 cm$^{-1}$; $^1$H NMR (DMSO-d$_6$) δ 8.61 (d, J=8.0 Hz, 1H), 8.22 (d, J=7.8 Hz, 1H), 8.05 (d, J=7.5 Hz, 1H), 7.83 (t, J=7.6 Hz, 1H) 7.56-7.43 (m, 4H), 5.02 (d, J=5.7 Hz, 1H), 4.80 (d, J=6.9 Hz, 1H), 4.75-4.45 (m, 2H), 4.51 (t, J=5.0 Hz, 1H), 4.41 (t, J=5.6 Hz, 1H), 4.24 (d, J=7.5 Hz, 1H), 4.10-4.00 (br m, 1H), 3.83 (t, J=7.6 Hz, 1H), 3.64-3.39 (m, 4H); CIMS m/z (rel. intensity) 248 [(MH$^+$—C$_6$H$_{12}$O$_5$), 100], 412 (MH$^+$, 15). Anal. Calcd for C$_{22}$H$_{21}$NO$_7$.0.8H$_2$O: C, 62.05; H, 5.35; N, 3.29. Found: C, 61.73; H, 5.08; N, 3.19.

Example (2'S,3'R,4'S,5'R)-5,6-Dihydro-6-(2',3',4',5'-tetrahydroxypentyl)-5,11-dioxo-11H-indeno[1,2-c]isoquinoline (17g). From lactone 16 (0.319 g, 1.29 mmol) and amine 15g (0.797 g, 4.40 mmol), in MeOH (90 mL), the general procedure afforded the desired product as an orange solid (0.041 g, 8%): mp 261-265° C. IR (KBr) 3419, 2951, 1971, 1697, 1610, 1573, 1547, 1501, 1458, 1421, 1320, 1268 cm$^{-1}$; $^1$H NMR (DMSO-d$_6$) δ 8.62 (d, J=8.1 Hz, 1H), 8.22 (d, J=8.1 Hz, 2H), 7.85 (t, J=7.2 Hz, 1H), 7.44-7.58 (m, 4H), 4.88 (d, J=3.9 Hz, 1H), 4.78 (d, J=6.1 Hz, 1H), 4.66-4.62 (m, 1H), 4.53-4.46 (m, 2H), 4.37-4.33 (m, 1H), 4.26 (d, J=6.5 Hz, 1H), 4.15-4.13 (m, 1H), 3.81 (q, J=6.2 Hz, 1H), 3.58-3.42 (m, 4H); EIMS m/z (rel. intensity) 247 [(M-C$_6$H$_{12}$O$_5$)$^+$, 100], 411 (M$^+$, 2). Anal. Calcd for C$_{22}$H$_{21}$NO$_7$: C, 64.23; H, 5.14; N, 3.40. Found: C, 63.91; H, 5.09; N, 3.43.

Example (2'S,3'S,4'R,5'R)-5,6-Dihydro-6-(2',3',4',5',6'-pentahydroxyhexyl)-5,11-dioxo-11H-indeno[1,2-c]isoquinoline (17h). From lactone 16 (0.110 g, 0.440 mmol) and amine 15h (0.200 g, 1.10 mmol) in MeOH (30 mL), the general procedure afforded the title compound as an orange solid (0.045 g, 25%) after washing with H$_2$O (10 mL) and CHCl$_3$ (~200 mL): mp 201-205° C. IR (KBr) 3373, 1703, 1639, 1019, 1548, 1504, 1425, 1316, 1263, 1062, 758 cm$^{-1}$; $^1$H NMR (DMSO-d$_6$) δ 8.61 (d, J=8.1 Hz, 1H), 8.27 (d, J=7.3 Hz, 1H), 8.22 (d, J=8.0 Hz, 1H), 7.84 (t, J=8.2 Hz, 1H) 7.55-7.42 (m, 4H), 5.27 (d, J=5.1 Hz, 1H), 4.97 (d, J=5.3 Hz, 1H), 4.84 (d, J=4.4 Hz, 1H), 4.67 (d, J=5.8 Hz, 3H), 4.47 (t, J=5.6 Hz, 1H), 4.27-4.20 (m, 1H), 3.85-3.80 (m, 1H), 3.67-3.42 (m, 4H); negative ion ESIMS m/z (rel. intensity) 410 [(M+H$^+$)$^-$, 36]. Anal. Calcd for C$_{22}$H$_{21}$NO$_7$.1H$_2$O: C, 61.53; H, 5.40; N, 3.26. Found: C, 61.30; H, 5.25; N, 3.46.

Example (2'S,3'R,4'R,5'R)-5,6-Dihydro-6-(2',3',4',5',6'-pentahydroxyhexyl)-3-nitro-5,11-dioxo-11H-indeno[1,2-c]isoquinoline (19). From lactone 18 (0.040 g, 0.136 mmol) and amine 15c (0.062 g, 0.341 mmol) in MeOH (15 mL), the general procedure afforded the title compound as an orange solid (0.021 g, 34%) after concentrating, re-suspending in CHCl$_3$ (20 mL), filtering, and washing with CHCl$_3$ (~30 mL) and ether (~30 mL): mp 265-267° C. IR (KBr) 3401, 2934, 1713, 1649, 1615, 1559, 1505, 1426, 1334, 1076 cm$^{-1}$; $^1$H NMR (DMSO-d$_6$) δ 8.92 (d, J=2.4 Hz, 1H), 8.78 (d, J=8.8 Hz, 1H), 8.61-8.50 (m, 2H), 7.64-7.56 (m, 4H), 5.20 (d, J=5.0 Hz, 1H), 4.94 (d, J=6.5 Hz, 1H), 4.90-4.80 (m, 1H), 4.62-4.58 (m, 3H), 4.45 (t, J=5.0 Hz, 1H), 4.20-4.10 (m, 1H), 3.90-3.80 (m, 1H), 3.65-3.34 (m, 4H); negative ion ESIMS m/z (rel. intensity) 455 [(M+H$^+$)$^-$, 24], 291 [(M+H$^+$)—C$_6$H$_{12}$O$_5$,]$^-$, 100. Anal. Calcd for C$_{22}$H$_{21}$NO$_7$: C, 57.90; H, 4.42; N, 6.14. Found: C, 57.66; H, 4.66; N, 6.48.

Example (1'S)-5,6-Dihydro-6-(1'-hydroxy-2'-methylethyl)-5,11-dioxo-11H-indeno[1,2-c]isoquinoline (22a). From lactone 16 (0.100 g, 0.403 mmol) and alcohol 21a (0.108 g, 1.21 mmol) in CHCl$_3$ (30 mL), the general procedure afforded the desired product as a dark red solid (0.086 g, 71%) after extraction and washing with ether: mp 215-217° C. IR (KBr) 3061, 2980, 2937, 2890, 1658, 1575, 1457, 1418, 1262, 1171, 1017 cm$^{-1}$; $^1$H NMR (CDCl$_3$) δ 8.67 (d, J=8.1 Hz, 1H), 8.27 (d, J=8.1 Hz, 1H), 7.75 (t, J=7.0 Hz, 1H), 7.65-7.58 (m, 2H), 7.49-7.37 (m, 3H), 5.14-5.08 (m, 1H), 4.42-4.36 (m, 1H), 4.18-4.12 (m, 1H), 3.68 (dd, J=8.1, 3.7 Hz, 1H), 1.77 (d, J=7.0, 3H); negative ion ESIMS m/z (rel. intensity) 288 [(MH$^+$+H$_2$O, 100], 306 (MH$^+$, 12). Anal. Calcd for C$_{19}$H$_{15}$NO$_3$: C, 74.74; H, 4.95; N, 4.59. Found: C, 74.45; H, 4.78; N, 4.57.

Example (1'R)-5,6-Dihydro-6-(3'-hydroxy-1'-methylethyl)-5,11-dioxo-11H-indeno[1,2-c]isoquinoline (22b). From lactone 16 (0.100 g, 0.403 mmol) and alcohol 21b (0.108 g, 1.21 mmol) in CHCl$_3$ (30 mL), the general procedure afforded the desired product as a dark red solid (0.074 g, 60%) after extraction and washing with ether: mp 216-217° C. IR (KBr) 3390, 2978, 2941, 2891, 1698, 1659, 1610, 1548, 1500, 1421, 1374, 1047 cm$^{-1}$; $^1$H NMR (CDCl$_3$) δ 8.67 (d, J=8.1 Hz, 1H), 8.26 (d, J=8.0 Hz, 1H), 7.71 (td, J=7.0 Hz, 1.3 Hz, 1H), 7.65-7.59 (m, 2H), 7.48-7.39 (m, 3H), 5.13-5.08 (m, 1H), 4.46-4.37 (m, 1H), 4.18-4.11 (m, 1H) 3.71 (dd, J=8.0, 3.9 Hz, 1H), 1.77 (d, J=7.0 Hz, 3H); ESIMS m/z (rel. intensity) 288 [(MH$^+$+H$_2$O)$^+$, 100], 306 (MH$^+$, 84). Anal. Calcd for C$_{19}$H$_{15}$NO$_3$.0.8H$_2$O.0.05 CHCl$_3$: C, 70.25; H, 5.15; N, 4.30. Found: C, 70.12; H, 4.76; N, 4.01.

Example (1'RS)-5,6-Dihydro-6-(3'-hydroxy-2'-methylethyl)-5,11-dioxo-11H-indeno[1,2-c]isoquinoline (22c). From lactone 16 (0.100 g, 0.403 mmol) and alcohol 21c (0.108 g, 1.21 mmol) in CHCl$_3$ (30 mL), the general procedure afforded the desired product as a dark red solid (0.077 g, 63%) after extraction and washing with ether: mp 225-227° C. IR (KBr) 3399, 2985, 2881, 1659, 1612, 1423 cm$^{-1}$; $^1$H NMR (DMSO-d$_6$) δ 8.59 (d, J=8.1 Hz, 1H), 8.18 (d, J=8.1 Hz, 1H), 7.89 (d, J=7.8 Hz, 1H), 7.81 (td, J=7.7 Hz, 1.3 Hz, 1H), 7.61-7.47 (m, 4H), 5.05 (t, J=5.8 Hz, 2H), 4.32-4.28 (m, 1H), 3.82-3.78 (m, 1H), 1.64 (d, J=6.8, 3H); ESIMS m/z (rel. intensity) 288, [(MH$^+$+H$_2$O)$^+$, 83], 306 (MH$^+$, 5). Anal. Calcd for C$_{19}$H$_{15}$NO$_3$: C, 74.74; H, 4.95; N, 4.59. Found: C, 74.39; H, 5.12; N, 4.43.

Example (2'RS)-5,6-Dihydro-6-[2'-hydroxy-3'-tert-(butyldiphenylsilyloxy)propyl]-5,11-dioxo-11H-indeno[1,2-c]isoquinoline (23). Compound 12c (0.350 g, 1.09 mmol) was dissolved in CH$_2$Cl$_2$ (30 mL), and TBDPSCl (0.329 g, 1.20 mmol) was added. Triethylamine (0.121 g, 1.20 mmol) and a catalytic amount of 4-DMAP were added. The solution was allowed to stir at room temperature. After 18 h, the solution was diluted with CH$_2$Cl$_2$ (50 mL), washed with H$_2$O (3×30 mL), and dried over Na$_2$SO$_4$. The solution was concentrated under vacuum to yield a red oil. The oil was purified by flash column chromatography (SiO$_2$, up to 50:50 EtOAc-hexanes) to yield the desired product as a red solid (0.220 g, 60%): mp 163-165° C. IR (film) 3684, 3020, 2400, 1659, 1521, 1427, 1216 cm$^{-1}$; $^1$H NMR (DMSO-d$_6$) δ 8.61 (d, J=8.0 Hz, 1H), 8.23 (d, J=7.7 Hz, 1H), 8.07 (d, J=7.6 Hz, 1H), 7.85-7.79 (m, 1H), 7.70-7.66 (m 4H), 7.56-7.29 (m, 10H), 5.35 (d, J=5.2 Hz, 1H), 4.76-4.58 (m, 2H), 4.16-4.13 (m, 1H), 3.83 (d, J=4.7, 2H), 1.03 (s, 9H); ESIMS m/z (rel intensity) 1140 [(2MNa)$^+$, 100], 582 [(MNa)$^+$, 34], 560 (MH$^+$, 4). Anal. Calcd for C$_{35}$H$_{33}$NO$_4$Si: C, 75.10; H, 5.94; N, 2.50. Found: C, 75.17; H, 5.91; N, 2.51.

Example 5,6-Dihydro-6-[2'-oxo-3'-tert-(butyldiphenylsilyloxy) propyl]-5,11-dioxo-11H-indeno[1,2-c]isoquinoline (24). Indenoisoquinoline 23 (0.200 g, 0.358 mmol) was dissolved in CH$_2$Cl$_2$ (65 mL). N-Methylmorpholine-N-oxide (0.083 g, 0.715 mmol) and TPAP (5%, 0.006 g, 0.018 mmol) were added to the solution. The reaction mixture was allowed to stir at room temperature for 4.5 h. The mixture was then diluted with CHCl$_3$ (40 mL) and washed with H$_2$O (5×40 mL). The organic layers were dried over Na$_2$SO$_4$ and concentrated under vacuum to yield a brownish-red solid. The solid was flushed through SiO$_2$ with 40:60 EtOAc-hexanes, and the filtrate was concentrated under vacuum to yield the desired product as a brownish-red solid (0.161 g, 81%): mp 175-178° C. IR (film) 3401, 2091, 1665, 1551, 1503, 1428, 1315, 1112 cm$^{-1}$; $^1$H NMR (DMSO-d$_6$) δ 8.61 (d, J=8.0 Hz, 1H), 8.23 (d, J=8.0 Hz, 1H), 8.04 (d, J=7.6 Hz, 1H), 7.87 (t, J=8.0 Hz, 1H), 7.70-7.68 (m, 4H), 7.60-7.39 (m, 11H), 5.64 (s, 2H), 4.83 (s, 2H), 1.03 (s, 9H); ESIMS m/z (rel. intensity) 558 (MH$^+$, 52). Anal. Calcd for C$_{35}$H$_{33}$NO$_4$Si.1.3H$_2$O: C, 72.34; H, 5.83; N, 2.41. Found: C, 72.29; H, 5.63; N, 2.59.

Example 5,6-Dihydro-6-(3'-hydroxy-2'-oxopropyl)-5,11-dioxo-11H-indeno[1,2-c]isoquinoline (25). Acetyl chloride (0.07 mL) was added dropwise to MeOH (1.8 mL). The resulting methanolic HCl was cooled to 20° C., and a solution of ketone 24 (0.030 g, 0.054 mmol) in CH$_2$Cl$_2$ (2 mL) was added. The reaction mixture was allowed to stir for 22 h. The solution was concentrated under vacuum and diluted with CHCl$_3$ (20 mL). The organic layer was washed with H$_2$O (4×15 mL), dried over Na$_2$SO$_4$, and concentrated under vacuum to yield an orange solid. The solid was purified by flash column chromatography (SiO$_2$), eluting with a gradient of 10% EtOAc in hexanes to EtOAc, to yield the desired product as an orange powder (0.006 g, 34%): mp 211-213° C. IR (film) 3435, 3020, 2400, 1729, 1708, 1658, 1550, 1504, 1427, 1215 cm$^{-1}$; $^1$H NMR (DMSO-d$_6$) δ 8.62 (d, J=8.3 Hz, 1H), 8.22 (d, J=7.9 Hz, 1H), 7.90 (t, J=7.9 Hz, 1H), 7.58-7.48 (m, 5H), 5.79 (t, J=6.0 Hz, 1H), 5.65 (s, 2H), 4.48 (d, J=6.1 Hz, 2H); CIMS m/z (rel intensity) 248 [(MH$^+$—C$_3$H$_4$O$_2$)$^+$ 100], 320 (MH$^+$, 65). Anal. Calcd for C$_{19}$H$_{13}$NO$_4$.0.4H$_2$O: C, 69.89; H, 4.26; N, 4.29. Found: C, 69.53; H, 4.01; N, 4.20.

Example (2'R)-5,6-Dihydro-6-(2'-hydroxypropyl)-5,11-dioxo-11H-indeno[1,2-c]isoquinoline (27a). From lactone 16 (0.100 g, 0.403 mmol) and alcohol 26a (0.091 g, 1.21 mmol) in CHCl$_3$ (30 mL), the general procedure was followed to afford the title compound as a red solid (0.074 g, 61%) after washing with ether: mp 176-180° C. IR (KBr) 3484, 2969, 2924, 1706, 1610, 1424 cm$^{-1}$; $^1$H NMR (DMSO-d$_6$) δ 8.61 (d, J=7.8 Hz, 1H), 8.23 (d, J=8.1 Hz, 1H), 7.93 (d, J=7.5 Hz, 1H), 7.85-7.80 (m, 1H), 7.59-7.47 (m, 4H), 5.11 (d, J=4.8 Hz, 1H), 4.51-4.38 (m, 2H), 4.10-4.00 (m, 1H), 1.27 (d, J=6.2 Hz, 3H); CIMS m/z (rel intensity) 306 (MH$^+$, 100). Anal. Calcd for C$_{19}$H$_{15}$NO$_3$.0.3H$_2$O: C, 73.44; H, 5.06; N, 4.51. Found: C, 73.06; H, 5.22; N, 4.38.

Example (2'S)-5,6-Dihydro-6-(2'-hydroxypropyl)-5,11-dioxo-11H-indeno[1,2-c]isoquinoline (27b). From lactone 16 (0.100 g, 0.403 mmol) and alcohol 26b (0.091 g, 1.21 mmol) in CHCl₃ (30 mL), the general procedure was followed to afford the title compound as a red solid (0.101 g, 82%) after washing with ether: mp 185-188° C. IR (KBr) 3484, 3068, 2970, 1708, 1648, 1574, 1503, 1423, 1317, 1266, 1196, 1064 cm$^{-1}$; $^1$H NMR (CDCl₃) 8.56 (d, J=8.1 Hz, 1H), 8.26 (d, J=8.1 Hz, 1H), 7.66-7.29 (m, 6H), 4.60-4.52 (m, 2H), 4.48-4.41 (m, 1H), 3.12 (d, J=5.1 Hz, 1H), 1.49 (d, J=6.2 Hz, 3H); negative ion ESIMS m/z (rel intensity) 306 (MH⁺, 37), 288 [(MH⁺+H₂O)⁺, 100]. Anal. Calcd for C₁₉H₁₅NO₃: C, 74.74; H, 4.95; N, 4.59. Found: C, 74.53; H, 5.13; N, 4.43.

Example (2'RS)-5,6-Dihydro-6-(2'-hydroxypropyl)-5,11-dioxo-11H-indeno[1,2-c]isoquinoline (27c). From lactone 16 (0.100 g, 0.403 mmol) and alcohol 26c (0.091 g, 1.21 mmol) in CHCl₃ (30 mL), the general procedure was followed to afford the title compound as an orange solid (0.108 g, 87%) after washing with ether: mp 191-194° C. IR (KBr) 3474, 2975, 2917, 1706, 1610, 1424 cm$^{-1}$; $^1$H NMR (DMSO-d₆) δ 8.60 (d, J=8.0 Hz, 1H), 8.22 (dd, J=8.1, 0.71 Hz, 1H), 7.91 (d, J=7.4 Hz, 1H), 7.84-7.78 (m, 1H), 7.59-7.44 (m, 4H), 5.11 (d, J=4.8 Hz, 1H), 4.53-4.31 (m, 2H), 4.10-4.00 (m, 1H), 1.25 (d, J=6.3 Hz, 3H); CIMS m/z (rel intensity) 306 (MH⁺, 100). Anal. Calcd for C₁₉H₁₅NO₃: C, 74.74; H, 4.95; N, 4.59. Found: C, 74.75; H, 5.14; N, 4.40.

Example (2'RS)-5,6-Dihydro-6-(3'-amino-2'-hydroxypropyl)-5,11-dioxo-11H-indeno[1,2-c]isoquinoline (27d). From lactone 16 (0.100 g, 0.403 mmol) and alcohol 26d (0.109 g, 1.21 mmol) in CHCl₃ (30 mL), the general procedure was followed to afford the title compound as an orange solid (0.107 g, 83%) after washing with ether: mp 185-188° C. IR (KBr) 3359, 1673, 1547, 1505, 1427 cm$^{-1}$; $^1$H NMR (DMSO-d₆) δ 8.69 (d, J=8.0 Hz, 1H), 8.21 (d, J=8.1 Hz, 1H), 8.04 (d, J=7.9 Hz, 1H), 7.83 (t, J=7.2 Hz, 1H), 7.57-7.41 (m, 4H), 4.60-4.30 (m, 2H), 3.90-3.80 (m, 1H), 2.80-2.65 (m, 2H); the hydroxyl and primary amino group are not visible due to exchange with residual water; ESIMS m/z (rel intensity) 321 (MH⁺, 100). Anal. Calcd for C₁₉H₁₅N₂O₃.1.2H₂O: C, 66.73; H, 5.42; N, 8.19. Found: C, 67.04; H, 5.30; N, 7.85.

Example (2'S)-5,6-Dihydro-6-(2',3'-dihydroxypropyl)-2,3-dimethoxy-5,11-dioxo-11H-indeno[1,2-c]isoquinoline (29). From lactone 28 (0.100 g, 0.324 mmol) and alcohol 20a (0.059 g, 0.628 mmol) in MeOH (30 mL), the general procedure was followed to afford the title compound as a red solid (0.051 g, 41%): mp 220-222° C. IR (KBr) 3402, 2965, 2928, 1697, 1632, 1479, 1429, 1396, 1263 cm$^{-1}$; $^1$H NMR (DMSO-d₆) δ 8.01 (s, 1H), 7.99 (d, J=7.8 Hz, 1H), 7.54-7.39 (m, 4H), 5.11 (d, J=5.1 Hz, 1H), 4.97-4.95 (m, 1H), 4.57-4.51 (m, 2H), 4.94-4.90 (m, 1H), 3.96 (s, 3H), 3.87 (s, 3H), 3.57-3.54 (m, 2H); ESIMS m/z (rel intensity) 382 (MH⁺, 100). Anal. Calcd. for C₂₁H₁₉NO₆: C, 66.13; H, 5.02; N, 3.67. Found: C, 65.77; H, 5.10; N, 3.59.

Example (2'S)-5,6-Dihydro-6-(2',3'-dihydroxypropyl)-3-nitro-5,11-dioxo-11H-indeno[1,2-c]isoquinoline (30). From lactone 18 (0.215 g, 0.733 mmol) and alcohol 20a (0.200 g, 2.20 mmol) in MeOH (60 mL), the general procedure was followed to afford the title compound as a yellow solid (0.171 g, 43%): mp 254-256° C. IR (KBr) 3320, 2946, 1714, 1659, 1613, 1502, 1425, 1333, 1201 cm$^{-1}$; $^1$H NMR (DMSO-d₆) δ 8.88 (d, J=2.3 Hz, 1H), 8.75 (d, J=9.0 Hz, 1H), 8.59-8.55 (m, 1H), 8.18 (d, J=7.1 Hz, 1H), 7.64-7.53 (m, 3H), 5.19 (d, J=5.0 Hz, 1H), 5.06 (t, J=5.0 Hz, 1H), 4.60-4.50 (m, 2H), 4.10-4.00 (m, 1H), 3.64 (t, J=4.9 Hz, 2H); negative ion ESIMS m/z (rel intensity) 365 [(M+H⁺)⁻, 89]. Anal. Calcd. for C₁₉H₁₄N₂O₆: C, 62.30; H, 3.85; N, 4.59. Found: C, 61.93; H, 3.86; N, 7.48.

Example

Topoisomerase I-Mediated DNA Cleavage Reactions. Human recombinant Top1 was purified from Baculovirus as previously described. DNA cleavage reactions were prepared as previously reported [Antony, S., et al., *Cancer Res.* 2007, 67, 10397-10405.] (for review see [Dexheimer, T. S. and Pommier, Y., *Nat. Protocol.* 2008, 3, 1736-1750.]) with the exception of the DNA substrate. Briefly, a 117-bp DNA oligonucleotide (Integrated DNA Technologies) encompassing the previous identified Top1 cleavage sites identified in the 161-bp fragment from pBluescript SK(−) phagemid DNA was employed. This 117-bp oligonucleotide contains a single 5'-cytosine overhang, which was 3'-end labeled by fill-in reaction with [α-$^{32}$P]-dGTP in React 2 buffer (50 mM Tris-HCl, pH 8.0, 100 mM MgCl₂, 50 mM NaCl) with 0.5 units of DNA polymerase I (Klenow fragment, New England BioLabs). Unincorporated [32]P-dGTP was removed using mini Quick Spin DNA columns (Roche, Indianapolis, Ind.), and the eluate containing the 3'-end-labeled DNA substrate was collected. Approximately 2 nM of radiolabeled DNA substrate was incubated with recombinant Top1 in 20 μL of reaction buffer [10 mM Tris-HCl (pH 7.5), 50 mM KCl, 5 mM MgCl₂, 0.1 mM EDTA, and 15 μg/mL BSA] at 25° C. for 20 min in the presence of various concentrations of compounds. The reactions were terminated by adding SDS (0.5% final concentration) followed by the addition of two volumes of loading dye (80% formamide, 10 mM sodium hydroxide, 1 mM sodium EDTA, 0.1% xylene cyanol, and 0.1% bromphenol blue). Aliquots of each reaction were subjected to 20% denaturing PAGE. Gels were dried and visualized by using a Phosphoimager and ImageQuant software (Molecular Dynamics). For simplicity, cleavage sites were numbered as previously described in the 161-bp fragment.

Example

Docking and Modeling Studies. Crystal structure preparation. The crystal structure of a ternary complex containing topoisomerase I, DNA, and topotecan, was downloaded from the Protein Data Bank (PDB ID 1K4T). This crystal structure was used due to the presence of co-crystallized water. The open carboxylate form, an atom of Hg, and molecule of PEG were deleted, and hydrogens were added in SYBYL 8.3.

A "mutant" crystal structure, containing the correct cleavage site for an indenoisoquinoline, was prepared by substituting the flanking (−1) A-T pair of this "prepared" structure with a G-C pair. The adenine→guanine mutation was performed using the "Mutate Monomers" function of SYBYL. The thymine→cytosine mutation was performed by manually changing the atom types. The energies of these two base pairs were subsequently minimized (with all other structures frozen in an aggregate) using the standard Powell method, the MMFF94 force field and MMFF94s charges, a distance-dependant dielectric function, and a 0.05 kcal/mol*Å energy gradient convergence criterion. The ternary complex centroid coordinates for docking were defined using the crystallized ligand as the center of the binding pocket (x=21.3419, y=−3.9888, z=28.2163). This ligand was then deleted.

Example

Docking validation. To validate the docking protocol, the crystal structures of camptothecin (PDB ID 1T8I), and an indenoisoquinoline (PDB ID 1SC7) were downloaded, and their respective ligands were extracted. The ligand from the topotecan structure was extracted as well and used for validations. For topotecan and campothecin, several atom types in the quinoline ring were reset from type C.2 to type C.Ar. For the indenoisoquinoline, the carboxyl group was fixed according to SYBYL atom types. Hydrogens were added to all ligands, and minimization was performed using the MMFF94 force field with MMFF94s charges, using a conjugate gradient method, distance-dependent dielectric function, and converging to 0.01 kcal/mol*Å. Docking was performed with GOLD 3.2 using default parameters and the coordinates defined by the crystal structure as described above. The top-ranked GOLD poses for each ligand were all within 1.5 Å RMSD. The top pose for each ligand was merged into the mutant crystal structure, and minimization was subsequently performed on a sphere with a radius of 6 Å containing the ligand. These structures were allowed to move during the minimization. The surrounding structures were frozen in an aggregate. Minimization were performed using the standard Powell method, the MMFF94 force field and MMFF94s charges, a distance-dependant dielectric function, and a 0.05 kcal/mol*Å energy gradient convergence criterion. These final minimized complexes were then compared to the original structures for camptothecin, topotecan, and the indenoisoquinoline MJ238 by aligning the proteins using the 'Align Structures by Homology' tool in SYBYL, using the alpha-carbons as the reference point. The resulting GOLD and crystal structure poses were compared using the smart_rmsd function in GOLD. The correct binding modes were observed in all cases. RMSD values were as follows: topotecan, 0.699 Å, camptothecin, 1.20 Å, indenoisoquinoline, 2.27 Å (likely higher due to the flexible side chain). Virtually identical results were obtained when the validation ligands were constructed de novo in SYBYL.

Example

Modeling of Indenoisoquinolines. Indenoisoquinolines 12a and 12b were constructed in SYBYL. Hydrogens were added, and the ligands were minimized using either the MMFF94 force field with MMFF94 charges, or the Tripos force field with Gasteiger-Huckel charges. Each ligand (two per charge set, four total) was docked into the mutant crystal structure using GOLD 3.2 using default parameters and the coordinates defined by the crystal structure as described above. The top three poses for each ligand were examined, and both the normal (compounds 12a and 12b) and flipped (compound 12a only) ligands were merged into the crystal structure, and the entire complex was subsequently subjected to minimization using a standard Powell method, the MMFF94 force field and MMFF94s charges, a distance-dependant dielectric function, and a 0.05 kcal/mol*Å energy gradient convergence criterion. The ligand overlays in FIG. 2 were constructed by aligning the crystal structures of 1SC7 and 1SEU using the 'Align Structures by Homology' function with the alpha-carbons as the reference.

28. The compound of claim 26, wherein said compound is
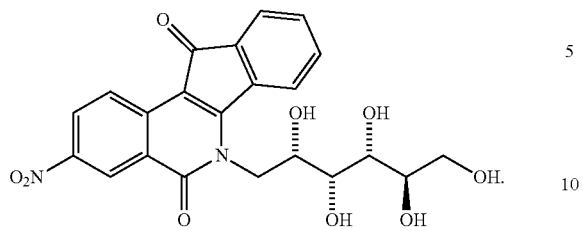

What is claimed is:
1. A compound of the formula

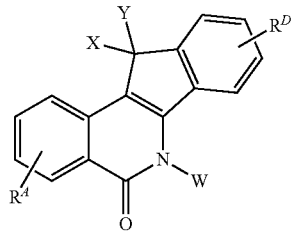

or a pharmaceutically acceptable salt thereof, wherein
$R^A$ represents four substituents each independently selected from the group consisting of hydrogen, halo, azido, and nitro, and hydroxy, amino, and thio, and acyl, sulfoxyl, sulfonyl, phosphinyl, and phosphonyl, and $CO_2H$, $SO_2H$, $SO_3H$, $PO_2H$, and $PO_3H$, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^A$ represents at least two adjacent substituents that are taken together with the attached carbons to form an optionally substituted heterocycle;

$R^D$ represents three substituents each independently selected from the group consisting of hydrogen, halo, azido, and nitro, and hydroxy, amino, and thio, and acyl, sulfoxyl, sulfonyl, phosphinyl, and phosphonyl, and $CO_2H$, $SO_2H$, $SO_3H$, $PO_2H$, and $PO_3H$, and alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, and arylalkynyl, each of which is optionally substituted; or $R^D$ represents at least two adjacent substituents that are taken together with the attached carbons to form an optionally substituted heterocycle;

X and Y are each independently selected from the group consisting of hydrogen, hydroxy, amino, hydroxylamino, and hydrazino, and alkyl, heteroalkyl, cycloalkyl, cycloheteroalkyl, aryl, and arylalkyl, each of which is optionally substituted; or X and Y are taken together with the attached carbon to form carbonyl, imino, oximino, hydrazono, and alkylidenyl, each of which is optionally substituted; and W is a secondary or tertiary branched alkanol or cyclic alkanol or W is a ketone.

2. The compound of claim 1 wherein W is a polyhydroxyalkane, or a diol, or a carbohydrate, or a sugar alcohol, or a $C_3$-$C_6$ sugar alcohol, or a $C_4$-$C_6$ sugar alcohol, or a $C_5$-$C_6$ sugar alcohol.

3. The compound of claim 1 wherein W includes a branched alkyl.

4. The compound of claim 1 wherein W is $CH_2CH(OH)$—R, where R is alkyl, heteroalkyl, cycloalkyl, cycloheteroalkyl, carbaryl, carbarylalkyl, heteroaryl, or heteroarylalkyl, each of which is optionally substituted.

5. The compound of claim 1 wherein W is $CH_2CH(OH)$—$CH(OH)$—R, where R is hydrogen, alkyl, heteroalkyl, cycloalkyl, cycloheteroalkyl, carbaryl, carbarylalkyl, heteroaryl, or heteroarylalkyl, each of which is optionally substituted.

6. The compound of claim 1 wherein W is a ketoalkanol.

7. The compound of claim 1 wherein W further includes an amino group.

8. The compound of claim 1 wherein W includes the following divalent radical

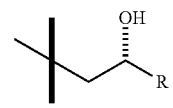

where R is alkyl, alkenyl, alkynyl, heteroalkyl, heteroalkenyl, heteroalkynyl, cycloalkyl, cycloalkenyl, cycloheteroalkyl, cycloheteroalkenyl, aryl, arylalkyl, arylalkenyl, or arylalkynyl, each of which is optionally substituted.

9. The compound of claim 1 wherein W is a hydroxy ketone.

10. The compound of claim 1 wherein W is a hydrogen bond forming group.

11. The compound of claim 1 wherein W is capable of forming one or more hydrogen bonds with residues in the DNA major groove.

12. The compound of claim 1 wherein W is capable of forming a hydrogen bond with Asn352 of a topoisomerase I.

13. The compound of claim 1 wherein $R^A$ represents four substituents each independently selected from the group consisting of hydrogen, halo, and nitro, and hydroxy, amino, and thio, and acyl, sulfoxyl, and sulfonyl, and $CO_2H$, and $SO_2H$, and alkyl, heteroalkyl, cycloalkyl, cycloheteroalkyl, carbaryl, carbarylalkyl, heteroaryl, and heteroarylalkyl, each of which is optionally substituted; or $R^A$ represents at least two adjacent substituents that are taken together with the attached carbons to form an optionally substituted heterocycle.

14. The compound of claim 1 wherein $R^A$ represents four substituents each independently selected from the group consisting of, halo, and nitro, and hydroxy, amino, and thio, and acyl, sulfoxyl, and sulfonyl, and $CO_2H$, and alkyl, heteroalkyl, cycloalkyl, cycloheteroalkyl, carbaryl, carbarylalkyl, heteroaryl, and heteroarylalkyl, each of which is optionally substituted.

15. The compound of claim 1 wherein $R^A$ represents two adjacent substituents that are taken together with the attached carbons to form an optionally substituted heterocycle.

16. The compound of claim 1 wherein $R^D$ represents four substituents each independently selected from the group consisting of hydrogen, halo, and nitro, and hydroxy, amino, and thio, and acyl, sulfoxyl, and sulfonyl, and $CO_2H$, and $SO_2H$, and alkyl, heteroalkyl, cycloalkyl, cycloheteroalkyl, carbaryl, carbarylalkyl, heteroaryl, and heteroarylalkyl, each of which is optionally substituted; or $R^D$ represents at least two adjacent substituents that are taken together with the attached carbons to form an optionally substituted heterocycle.

17. The compound of claim 1 wherein $R^D$ represents four substituents each independently selected from the group consisting of, halo, and nitro, and-hydroxy, amino, and thio, and acyl, sulfoxyl, and sulfonyl, and $CO_2H$, and alkyl, heteroalkyl, cycloalkyl, cycloheteroalkyl, carbaryl, carbarylalkyl, heteroaryl, and heteroarylalkyl, each of which is optionally substituted.

18. The compound of claim 1 wherein $R^D$ represents two adjacent substituents that are taken together with the attached carbons to form an optionally substituted heterocycle.

19. The compound of claim 1 wherein at least one of $R^A$ is nitro, or alkoxy or, methoxy.

20. The compound of claim 1 wherein at least two of $R^A$ are bismethoxy, or alkyleneoxy, or methyleneoxy.

21. The compound of claim 1 wherein at least one of $R^D$ is nitro, or alkoxy, or methoxy.

22. The compound of claim 1 wherein at least two of $R^D$ are bismethoxy, or alkylenedioxy, or methylenedioxy.

23. The compound of claim 1 wherein X and Y are taken together with the attached carbon to form carbonyl.

24. A pharmaceutical composition comprising one or more compounds of claim 1 and one or more carriers, diluents, or excipients, or a combination thereof for treating cancer.

25. A method for treating cancer, the method comprising the step of administering to a patient in need of relief from the cancer a composition comprising a therapeutically effective amount of one or more compounds of claim 1 and one or more carriers, diluents, or excipients, or a combination thereof.

26. The compound of claim 1, wherein said compound has the following formula:

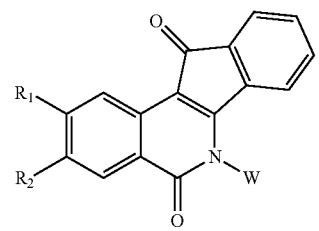

wherein $R_1$ is hydrogen or methoxy;

$R_2$ is hydrogen, methoxy, or nitro; and

W is selected from the group consisting of

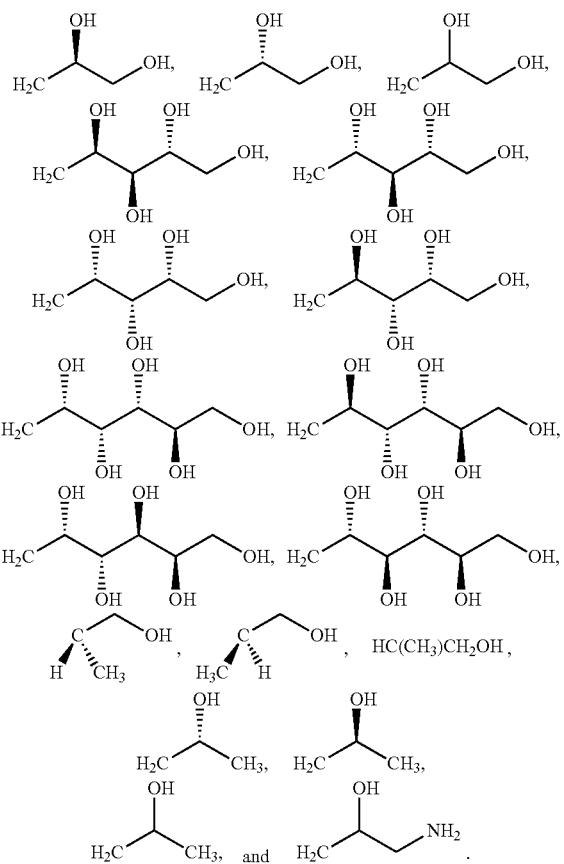

27. The compound of claim 26, wherein said compound is

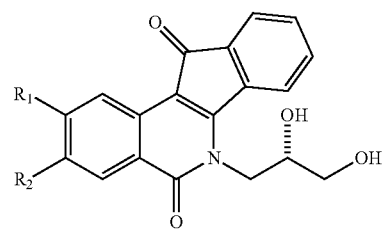

wherein $R_1$ is hydrogen and $R_2$ is nitro.